United States Patent [19]

Massie et al.

[11] Patent Number: 5,518,913
[45] Date of Patent: May 21, 1996

[54] HIGH LEVEL RECOMBINANT PROTEIN PRODUCTION USING CONDITIONAL HELPER-FREE ADENOVIRUS VECTOR

[75] Inventors: Bernard Massie, Laval; Yves Langelier, Montreal, both of Canada; Natalie Lamarche, London, United Kingdom

[73] Assignee: National Research Council of Canada, Ottawa, Canada

[21] Appl. No.: 232,998

[22] Filed: Apr. 22, 1994

Related U.S. Application Data

[63] Continuation-in-part of Ser. No. 58,800, May 10, 1993, abandoned, which is a continuation of Ser. No. 774,223, Oct. 10, 1991, abandoned.

[51] Int. Cl.$^6$ .............................. C12N 7/01; C12N 15/85
[52] U.S. Cl. ...................... 435/235.1; 435/320.1
[58] Field of Search ............................... 435/320.1, 235.1

[56] References Cited

PUBLICATIONS

Lamarche et al. (1990), J. Gen. Virol. 71:1785–1792.
Leong et al. (1990), J. Virol. 64(1):51–60.
Berg et al. (1988), Nucl. Acids Res. 16(18):9057.

*Primary Examiner*—Mindy Fleisher
*Assistant Examiner*—Philip W. Carter
*Attorney, Agent, or Firm*—Hodgson, Russ, Andrews, Woods & Goodyear

[57] ABSTRACT

The present invention relates to methods and compositions involving an improved recombinant transfer vector for introducing a DNA sequence, encoding a recombinant protein, into an adenovirus genome in generating recombinant adenovirus. Recombinant protein production, in cells infected with the recombinant adenovirus, can approach levels as high as 15–20% of total cellular proteins. The improved transfer vector includes an expression cassette comprising sequentially a transcription promoter, a high efficiency leader, at least one splicing signal, an enhancer-like sequence, a cloning site and a plurality of polyadenylation sites.

4 Claims, 10 Drawing Sheets

HIGH LEVEL RECOMBINANT PROTEIN PRODUCTION USING CONDITIONAL HELPER-FREE ADENOVIRUS VECTOR

This application is a continuation-in-part of U.S. patent application Ser. No. 08/058,800 filed May 10, 1993 now abandoned, which was a continuation of U.S. patent application Ser. No. 07/774,223 filed Oct. 10, 1991, now abandoned, the disclosures of which are incorporated herein by reference.

FIELD OF THE INVENTION

The invention relates to adenovirus transfer vectors, particularly to transfer vectors allowing for the production in infected cells of recombinant proteins to a level as high as 15– 20% of total cellular proteins.

BACKGROUND OF THE INVENTION

Biological production of proteins through recombinant DNA technology has been one of the leading aspects in biotechnology research over the last decade. To achieve economically viable levels of expression while still obtaining a biologically active protein, both eukaryotic and prokaryotic systems have been studied. Prokaryotic systems typically utilize *Escherichia coli* as the bacterial host of choice for the expression of heterologous genes for both practical and economical considerations. However, the insertion of cloned DNA sequences into an expression unit does not guarantee efficient gene expression when the expression unit is introduced into the bacterial host cell.

Hence, despite the versatility and efficacy of its expression vectors, with levels of expression in the range of 20 to 50% of total cellular proteins, *E. coli* suffers several limitations for the expression of different categories of heterologous proteins especially those that undergo complex post-translational modifications such as many viral and mammalian proteins. Those limitations include inappropriate or lack of post-translational modifications, incorrect folding, proteolytic degradation, inefficient secretion and, recently reported, amino acid misincorporation.

Because of the limitations described above for *E. coli* expression systems, efforts have been directed towards the development of more sophisticated expression systems including other prokaryotes, lower eukaryotes such as yeast, and higher eucaryotes such as mammalian and insect cells. From the review of the vast literature reports on the expression of recombinant proteins appears to emerge the increasingly accepted notion that there is no "universal expression system". The current trends in the field is to tailor the development of expression systems to fit the specific expression needs. It is in that perspective that insect virus vectors and adenovirus vectors have been initially developed, mainly to exploit their respective capacity to express recombinant proteins in insect and human cells.

Poxvirus research, and more particularly the use of vaccinia virus, a prototypic member of the group of poxviruses, has led to eukaryotic cloning and expression of vectors useful in various biological and medical applications. In 1982, Panicali and Paoletti reported that endogenous subgenomic elements could be inserted into infectious progeny vaccinia virus via recombination in vivo (1982, *Proc. Natl. Acad. Sci. USA*, 1979: 4927–4931); and subsequently demonstrated that they could insert foreign genes into infectious vaccinia virus and obtain pure cultures of recombinant vaccinia virus expressing the foreign gene.

It was reported that vaccinia virus appear to have several advantages over other eukaryotic vectors. Most noteworthy was the fact that virus infectivity was not impaired by insertion and expression of foreign gene in contrast to defective SV40 and retrovirus vectors. Although, vaccinia virus has been successfully used as an expression vector through the insertion of foreign genes into a non-essential region of the viral genome via homologous recombination, some drawbacks have also been associated with the use of this virus. The most difficult problem appears to reside in the fact that vaccinia expression vectors are not capable of producing abundant foreign proteins because of the absence of known strong promoters.

Baculovirus vectors have also been used for the expression of foreign genes in insect cells. Indeed, in the case of baculovirus, two very strong and very late promoters are responsible for the expression of two extremely abundant proteins, polyhedrin and p10, which can together constitute as much as 50% of total cellular proteins in baculovirus-infected cells. *Autographa californica* nucleopolyhedrosis virus (AcNPV) is the prototype virus of the family Baculoviridae. This virus has a wide host range and infects a large number of species of lepidoptera insects.

AcNPV possesses several properties that make this virus ideally suited as an expression vector for cloned eukaryotic genes. Since occlusion of the virus is not absolutely essential for viral growth, the polyhedrin gene provides a non-essential region of the AcNPV genome in which foreign DNA may be inserted. Placing foreign genes of interest under the control of either the polyhedrin or the p10 promoter have led in the best cases to production of recombinant proteins at 20–25% of total cellular proteins. The rapid construction of efficient transfer vectors has also been facilitated by the relatively low complexity of gene regulation in the expression of the polyhedrin and p10 baculovirus genes.

Using the properties of AcNPV, a wide variety of eukaryotic and prokaryotic genes have been expressed successfully with baculovirus vectors in insect cells. However, expression levels for different genes inserted into the same vector are often different and are related to the length and nature of the leader sequence preceding the foreign gene. Even in the best available vectors, there is some variability in expression levels depending on factors such as the nature of the gene and the protein expressed. Furthermore, careful characterization of numerous recombinant proteins has pointed to some problems in post-translational modifications in insect cells, such as impaired glycosylation, incomplete proteolytic cleavage of polyprotein precursors, and inefficient secretion. This would appear to preclude the utilization of this expression system for the production of numerous complex mammalian proteins. In this regard, other alternatives better suited for the expression of mammalian proteins, such as adenovirus vectors, are being investigated.

Adenoviruses (Ad) have first been isolated over three decades ago. Since then, many efforts have been invested into defining their biological properties. The intimate association that these viruses have with their host during infection has potentiated their value as tools for exploring the mechanisms of macromoleculer biosynthesis in mammalian cells. The temporal pattern of adenovirus infection of human cells is generally demarcated by two phases of expression, early and late, which are separated by the onset of replication after about 8 hours of infcetion. Early in infection, at least 7 promoters are active, generating transcripts from early regions 1–4. Over 30 messages corresponding to the early regions have been identified by RNA analysis and/or cDNA cloning.

In contrast, the high levels of expression of the abundant viral late proteins are the result of the strong transcriptional activity of one promoter, the major late promoter (MLP) which is responsible for the production of some twenty late proteins encoded by an equivalent number of mRNAs. These mRNAs are all derived from one very long primary transcript by maturation processes involving differential splicing and polyadenylation events. Among those late proteins, three structural proteins, namely hexon (15–20% of total cellular proteins), fiber (8–10%), and penton (2–4%), and one non-structural protein named 100K (5–10%), constitute collectively as much as 35% of total cellular proteins in Ad-infected cells, whereas the remaining minor late proteins would constitute some 5%. FIG. 1 shows an autoradiogram of the late structural proteins metabolically labelled with $^{35}$S methionine from adenovirus infected 293 cells. The AdPyR39 recombinant was produced following the description provided by Massie et al. (1986, *Mol. Cell. Biology*, 6:2872–2883, hereby incorporated by reference). The relative abundance of these late viral proteins can fluctuate depending on infection conditions. However, little is known about the mechanism which regulates this phenomenon. In any case, only a small portion of the structural proteins which are synthesized in copious amount, 20–30% of the hexon and 1–5% of penton and fiber respectively, are assembled into functional nucleocapsids. Therefore, it was soon realized that appropriate manipulations of Ad genome could potentially result in the construction of Ad recombinants expressing foreign proteins at very high levels.

The first human adenovirus (Ad) vectors have been developed in the early 1980's. These vectors have been used to express a wide variety of viral and cellular genes (for a complete review, see Berkler, 1988, *Biotechniques* 6:616–629, hereby incorporated by reference). Currently, there are three potential commercial applications for Ad vectors, namely in 1) high level expression of heterologous proteins, 2) live viral sub-unit vaccines and 3) gene transfer vectors for establishing stable cell lines or gene therapy.

Adenovirus vectors appeared promising for expression of high levels of protein, since transcription from the major late promoter was so efficient and high levels of translation were accompanied by host protein synthesis shut-off late in infection, facilitating protein isolation. Furthermore, human adenoviruses can replicate efficiently to very high titers ($10^9$–$10^{10}$ pfu/ml) in human cells, as well as other mammalian cells; and adenoviruses produce their late proteins at levels than reach 30 to 40% of total cellular proteins. Finally, they can be propagated in suspension cultures thereby demonstrating a clear potential for large scale production.

The construction of helper-free Ad recombinants expressing foreign proteins at very high levels is generally accomplished by using MLP-based expression cassettes inserted in the deleted E1 region. The ectopic MLP sequences found in those expression cassettes have incorporated between 200 and 700 bp upstream, and 33 bp downstream of the transcriptional start site. Those sequences were expected to include all of the required elements that confer full transcriptional activity to the endogenous MLP. However, the majority of recombinant adenoviruses constructed thus far express only low to moderate levels of heterologous proteins. These levels are usually lower than the normal levels of adenovirus late proteins. Only a hand-full of examples of Ad recombinants were shown to express recombinant proteins at levels that rival the amount of some of the abundant adenoviral late proteins. Examples include AdSVR112 (Gluzman et al., 1982, *Eukaryotic Viral Vectors*, Cold Spring Harbor Laboratory Press, N.Y., pp. 187–192) which expresses the SV40 large T antigen at 3–4% of total cellular proteins; and Ad5-RR2$^{HSV}$ which expresses the HSV ribonucleotide reductase subunit 2 (R2) at 4–5% of total cellular proteins (Lamarche et al., 1990, *J. Gen. Virology*, 71:1785–1792, hereby incorporated by reference).

Also described in the literature are adenovirus recombinants that appear to produce foreign proteins at levels which are somewhat between the level at which the 100 K protein is produced and the level at which the fiber protein is produced, although no accurate quantitation was reported in those latter cases. Thus, it seems that none of these Ad recombinants succeeded in expressing their heterologous protein at a level equivalent to the level of hexon or fiber which are respectively the first and second most abundant proteins in Ad-infected cells. These attempts indicate that because of the complexity in the regulation of gene expression in adenoviruses, their full potential as high level expression vectors has yet to be realized.

A better understanding of the molecular mechanisms underlying the complex regulation of gene expression in adenoviruses is essential in order to construct transfer vectors which exploit the full potential for high level expression in this system. One example among the best recombinant cistron assembled so far for high level expression of foreign genes in adenovirus is represented in the transfer vector pAdBM1 (Lamarche et al., supra). In pAdBM1, the expression cassette includes sequentially: the strong major late promoter (MLP), a high efficiency translational leader (Ad2 tripartite leader), splicing signals, a cloning site, and multiple polyadenylation sites. Given that in Ad recombinants derived from pAdBM1 the ectopic MLP drives the expression of only one mRNA, whereas the endogenous MLP produces more than 20 mRNAs, one would have expected that the level of expression from the ectopic MLP would be equivalent to or approaching the sum of the late viral proteins. Since this has not been observed, it appeared reasonable to conclude that the MLP functions much less efficiently when taken out of its native environment. Whether a promoter structure similar to, or mimicking that of, the native MLP configuration could be obtained was not clear as the number of combinations in which a promoter could be linked to enhancers and other transcriptional and translational control elements is essentially infinite despite the finding by Leong et al. (1990, *J. Virology*, 64: 51–60) that sequences mapping between +30 and +130 have been shown to play a critical role in the induction of sequence-specific binding proteins by transcription of the Ad MLP during the late phase of infection.

The present invention relates to the development of an improved Ad expression system utilizing an improved and novel Ad expression vector termed pAdBM5. The construction of pAdBM5 included the introduction of enhancer sequences to further stimulate the transcriptional activity of the ectopic MLP.

Traditional enhancers are expression elements that have been described as having the following properties: 1) containing repeated sequences that can function independently; 2) acting over distances, sometimes considerable (even up to thousands of bases); 3) may function in either orientation; 4) may function in a position independent manner, and can be within or downstream of the transcribed region, but can only function in cis (if several promoters lie nearby, the enhancer may preferentially act on the closest); 5) may function in a cell type or tissue-specific manner (Kriegler, 1990, *Methods in Enzymology*, 185: 512–527). Studies, however, have shown that the properties of enhancers are even more highly varied and can function in a variety of ways. For example, the effects of the variation of position of the SV40 enhancer on the expression of multiple transcription units in a single plasmid revealed two types of position effects. One position effect is called promoter occlusion and results in reduced transcription at a downstream promoter if transcription is initiated at a nearby upstream promoter. This effect does not involve enhancer elements directly, even though the effect is most pronounced when the downstream promoter lacks an enhancer element. The second effect stems from the ability of promoter sequences to reduce the effect of a single enhancer element on other promoters in the same plasmid. Thus, according to Kriegler, the SV40 enhancer element is a complex structure whose function is subject to some position effects and whose cell-type-specific activation is dependent, in part, on the absence or presence of active cellular factors or proximal sequences.

Another example given by Kriegler is one of a viral enhancer described in the hepatitis B virus. This enhancer is located 3' to the hepatitis B virus surface antigen coding sequences but is contained within the mature viral transcripts. Authors have reported that the HBV enhancer can dramatically increase expression levels of genes controlled by the SV40 enhancer/promoter but only when the enhancer is located within the transcribed region of the gene. Further, this effect appears to be orientation dependent, a violation of already unsettled enhancer rules.

Thus, from previous studies, it would not be obvious to one skilled in the art how to use enhancers to increase transcription from the Ad MLP; i.e. it would have been difficult to predict what enhancer sequences may be used, or where or how it may be placed in the genome of a recombinant adenovirus vector to enhance expression levels.

Recently, it has been shown that a number of cis-acting sequences are essential to confer full transcriptional activity of the MLP during the late phase of infection (Mondésart et al., 1991, *Nucleic Acids Research* 19:3221–3228, hereby incorporated by reference). These include an upstream element (UE) between −67 and −49 relative to the transcriptional start site; a TATA box centered at −28; and an initiator element encompassing the transcription start site. In addition, some downstream elements (DE) have been mapped and designated, RI (+37 to +68), DE1 (+85 to +96) or R2 (+80 to +105), and DE2 (+109 to +124) or R3 (+105 to +125) (see FIG. 2). While the UE, the TATA box and the R1 downstream element have been shown to be important for basal transcriptional activity of the MLP both at early and late times, the DE (DE1 and DE2) would be essential for late phase specific activation. DE1 and DE2 are functionally redundant and probably bind to the same transcription factor(s). They may also interact synergistically with the UE by an unknown mechanism, to bring about their late phase specific transcriptional activation. At this point, it is not clear whether these cis-acting sequences are "enhancer-like" or downstream promoter elements and whether enhanced expression could be obtained by inserting them in a transfer vector. These sequences are missing in all of the MLP currently used in Ad transfer vectors described so far. The inherent difficulty in properly evaluating the position at which enhancer-like or downstream promoter elements could be inserted to enhance expression still remains to be solved.

SUMMARY OF THE INVENTION

In accordance with the present invention, there is provided a novel adenovirus recombinant transfer vector to be used in the production of higher levels, than have been achieved previously, of heterologous proteins in host cells. The high levels of expression are obtained through the use of at least one enhancer sequence, optionally conjugated to other enhancer sequences placed at specific regions on the adenovirus vector. Thus, the present invention relates to an improved recombinant transfer vector capable of introducing a DNA sequence encoding a recombinant protein into an adenovirus genome. The improved transfer vector includes an expression cassette comprising a cloning vehicle having a DNA sequence comprising sequentially a transcription promoter, a high efficiency leader, at least one splicing signal, an enhancer-like sequence, a cloning site, and a plurality of polyadenylation sites. The enhancer-like sequence is to be located between the high efficiency leader and the cloning site where the foreign gene is to be incorporated. Preferably, the enhancer-like sequence corresponds to the +30 to 130 AD2MLP sequence (described in Leong et al., 1990, supra, the contents of which is hereby incorporated by reference). In another preferred aspect of the present invention, the adenovirus vector may also include another enhancer-like sequence to be located immediately upstream from the transcription promoter.

The invention also relates to recombinant adenovirus capable of expressing a DNA sequence encoding a recombinant protein in mammalian cells, preferably in human cells. The recombinant adenovirus is an adenovirus genome comprising a DNA sequence encoding a recombinant protein and a DNA sequence comprising sequentially a transcription promoter, a high efficiency leader, at least one splicing signal, an enhancer-like sequence, a cloning site and a plurality of polyadenylation sites.

Also within the scope of the present invention is a method for producing recombinant adenovirus possessing the ability to express a DNA sequence encoding a recombinant protein in mammalian cells. The method comprises cleaving the improved transfer vector which comprises sequentially a transcription promoter, a high efficiency leader, at least one splicing signal, an enhancer-like sequence, a cloning site, and one or a plurality of polyadenylation sites; preparing a recombinant transfer vector by inserting into the linearized transfer vector a DNA fragment containing at least one DNA sequence encoding a recombinant protein into the thus modified transfer vector such that the DNA sequence encoding the heterologous protein is under the control of the transcription promoter; contacting the recombinant transfer vector with adenovirus DNA through homologous recombination; and isolating and recovering the desired recombinant adenovirus.

Also within the scope of the present invention is a method for synthesizing a recombinant protein which comprises: a) infecting mammalian host cells with a recombinant adenovirus that contains adenovirus genomic DNA, a DNA sequence encoding a recombinant protein, and a DNA sequence comprising sequentially a transcription promoter, a high efficiency leaders at least one splicing signal, an enhancer-like sequence, a cloning site and a plurality of polyadenylation sites; and b) growing the mammalian host cells and recovering the desired product.

With the construction of the improved adenovirus transfer vector of the present invention, unprecedented levels of recombinant gene expression have been achieved in preferred host cells such as human and mammalian cells. More preferably, human 293 cells infected with helper-free adenovirus recombinants generated with the best mode of the improved transfer vector of the present invention have produced recombinant proteins that represent the most abundant polypeptide in the cell (15–20% of total cellular proteins), at least equalling the level of the most abundant viral late protein, the hexon.

With the transfer vector of the present invention, commercial production of recombinant proteins from host cells infected with recombinant plasmids generated from this transfer vector is greatly improved. One major factor for the economical production of recombinant proteins in the adenovirus system lies in the possibility to produce recombinant proteins in suspension cultures. For example, the human 293, human K562 and the Hela cell lines or derivatives thereof, bearing the adenovirus E1 region which have been adapted to grow as suspensions, can be used preferentially. High levels of expression can also be achieved in other types of mammalian and human cells, but it is to be noted that the use of helpers may in some instances be necessary. In order to achieve these exceptional and economically viable levels of expression, it appears that the position in the transfer vector of the enhancer-like sequence, preferably the Ad2MLT enhancer-like sequence referred to previously, is critical. The present invention will be more readily illustrated by referring to the following description.

BRIEF DESCRIPTION OF THE FIGURES

FIG. 5 represents stained SDS-PAGE gels showing expression of HSV-2 R2 in 293 cells infected with recombinant Ad5BM1-R2 or Ad5BM5-R2. Also shown are molecular weight markers and the position of hexon, fiber, and R2 proteins.

FIG. 6 are representations showing expression of HSV-2 R1 in 293 cells infected with recombinant AdRed-1, Ad5BM1-R1 or Ad5BM5-R1. Also shown are molecular weight markers and the position of hexon, and R1 proteins.

FIG. 8 shows scale-up of the Ad expression system.

FIG. 9 shows quantification of R1 in soluble and pellet fractions of infected cell extracts.

DETAILED DESCRIPTION OF THE INVENTION

Figure 1:
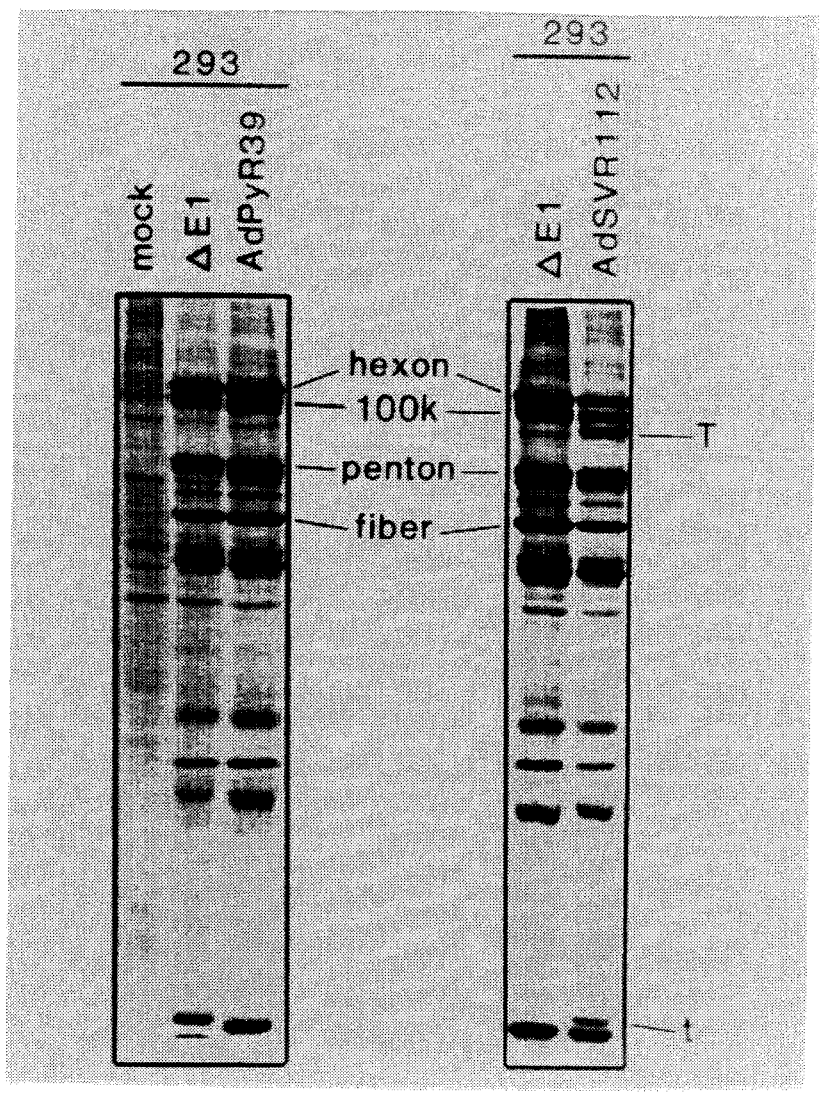
FIG. 1 represents an autoradiograph for relative quantitaion of total proteins extracted from cells infected by various adenovirus recombinants. 293 cells were infected with Ad5ΔE1/d1309, Ad5pYR39 or AdSVR112. At 20 hours after infection, cells were labeled for 2 hours with $^{35}S$ methionine. Total proteins were extracted, resolved by SDS-PAGE electrophoresis (10%), and revealed by autoradiography. The position of the Ad abundant late proteins, hexon, 100K, penton and fiber as well as recombinant SV40 large T antigen, are indicated.

The invention relates to an improved adenovirus transfer vector useful in achieving production of high levels of recombinant proteins in mammalian cells. The expression cassette of the transfer vector of the present invention includes a fragment which comprises sequentially a transcriptional promoter, a high efficiency leader, at least one splicing signal, a first enhancer-like sequence, a cloning site, and a plurality of polyadenylation sites. Preferably, the sequence also comprises a second enhancer-like sequence upstream from the transcriptional promoter and two 5' splice donor sites located upstream of the MLP enhancer-like sequence and one 3' splice acceptor site located immediately downstream. The presence of the second enhancer-like sequence appears to be optional as marginal enhancement in expression is obtained when it is present in the vector without the first enhancing-like sequence.

preferably, the adenoviral DNA, to be recombined with the improved transfer vector of the present invention in generating Ad recombinants, lacks the E3 coding region which is known to be dispensible for growth of the virus in cell cultures as well as the E1 coding region which encodes proteins essential for the activation of adenovirus promoters. The loss of the E1 region in the DNA is complemented by an appropriate mammalian cell line such as 293 cells which constitutively express the E1 protein from an integrated E1 (preferably Ad5E1) coding region. These deletions allow for the insertion of up to 7–8 kb of foreign DNA generating helper-free recombinant adenovirus. Adenovirus vectors are preferably suited for the expression of recombinant mammalian proteins, particularly but not exclusively of human origin.

Helper-free adenovirus recombinants generated with the transfer vector of the present invention are chosen to infect host cells in an appropriate medium. Preferably, the culture host cell is a mammalian host cell and more preferably, a human cell of the type described above.

Among the transcriptional promoters that may be used to prepare the improved transfer vector of the present inventions strong viral promoters are preferred because of their efficiency in directing transcription. However, other transcriptional promoters such as the mouse metallothionein (MT-1) promoter, the SV40 late promoter, the SV40 early promoter and cytomegalovirus (CMV) promoter may be used. A particularly preferred viral promoter is the major late promoter (MLP) from adenovirus.

The transfer vector of the present invention also includes a highly efficient leader immediately downstream from the transcriptional promoter. Preferred leader sequences are viral leader sequences which include the adenovirus first leader and the adenovirus L1-IX leader, the SV40 leader and the parvovirus leader. A particularly preferred leader sequence is the high efficiency viral leader, adenovirus tripartite leader (TPL).

The presence of efficient splicing sequences (5' and 3') that have been functionally shown to participate in an mRNA splicing event may also be required. Preferred splicing sequences include 5' donor sites of either the first or the third segment of the tripartite leader and 3' acceptor site from an immunoglobulin gene.

With regard to the polyadenylation sites, it seems that a plurality of sites is preferred in order to generate the highest possible level of the appropriate recombinant proteins. The number of sites may vary from 2 to 5 but it would appear that the preferred number of sites be 3. The polyadenylation sites that may be chosen for use in the transfer vector of the present invention may be selected from, but are not restricted to, the group consisting of SV40 early or late poly A signals, polyoma early poly A, Ad5 hexon mRNA poly A signals and β-globin poly A signal.

The preferred enhancer-like sequence to be introduced in the improved transfer vector of the present invention is a sequence normally located in the intron between the first and the second active sequence of the tripartite leader. In order to preserve the integrity of the tripartite leader, the enhancer-like sequence was relocated further downstream from its normal position. Preferably, the enhancer-like sequence is positioned about 303 nucleotides further downstream from its normal position in the Ad5 genome. This relocation of the enhancer-like sequence relative to its normal position in the Ad5 genome resulted in a 2.5 to 3 fold increase in recombinant protein expression when comparing a vector devoid of the enhancer-like sequence such as pAdBm1 (4–5% of total cellular proteins) with a vector bearing the enhancer-like sequence downstream from the tripartite leader such as pAdBM5 (to 15–20% of total cellular proteins). The enhancer-like sequence is specifically exemplified as SEQ ID NO:1, and described in Leong et al. (1990, supra). It is possible that other enhancer-like sequences may be used at a similar position. It is also preferred to use a second enhancer-like sequence immediately upstream of the transcription promoter. A preferred enhancer sequence is the BKV Dun enhancer sequence which is exemplified as SEQ ID NO:2 and described in Berg et al. (1988, *Nucleic Acids Research* 16: 9057, hereby incorporated by reference). Tests have been conducted using an enhancer sequence upstream from the promoter without an enhancing sequence between the tripartite leader and the cloning sites without noticing substantial improvement in expression yields. This indicates that either of the cis-acting first and second enhancer-like sequences, when used separately, is able to stimulate high level expression of recombinant protein with similar efficiency; however, not quite as efficiently as the combination of the two elements, suggesting a synergistic interaction between the two enhancer-like sequences.

The improved transfer vector of the present invention has wide application in the construction of recombinant adenoviruses for the production of recombinant proteins in mammalian cells. These applications include the production of commercial quantities of therapeutic and commercially important proteins. The vectors of the invention may be adapted to include sequences encoding proteins of interest and coding sequences which enhance or enable the expression of biologically active proteins of interest. It is important to note that the transcription of the foreign gene in the resulting recombinant adenovirus takes place in the opposite orientation from the overall direction of transcription of the late adenovirus genome. This is required because it has been shown previously in other adenovirus recombinants that expression in the same orientation as the overall direction of transcription can interfere with the normal expression of other adenoviral genes in the downstream E1b region.

The Ad recombinants of the present invention may be introduced into host cells by infection using methods described in the prior art. An example is the method described by Lamarche et al. (supra). Various mammalian host cells can be used in the context of the present invention. Examples of mammalian cells include human cells and bovine cells. Suitable mammalian cell lines include the 293 (ATCC 1573) cell line, or Hela and K562 cell lines, as well as derivatives expressing AdE1, and isolates of these cell lines, although it will be obvious to those skilled in the art that other cell lines may be preferred for the production of particular proteins. The host cell line should be selected on the basis of its ability to produce the protein of interest at a high level and/or its suitability for very specific post-transitional modification of the desired protein.

It was found that when using the best mode of the improved transfer vector of the present invention (pAdBM5, having been deposited with the American Type Culture Collection in accordance with the terms of the Budapest Treaty, and bearing ATCC Designation 75704), the recombinant adenovirus replicated efficiently to levels close to $5 \times 10^9$ pfu/ml. It is to be noted that excessive expression levels may in some instances reduce the virus titer below acceptable levels. With the present invention, it appears that the very high level of production of recombinant protein takes place at the expense of the Ad abundant late proteins. However, in the case of Ad5BM5-R2 and Ad5BM5-R1 recombinants that illustrate preferred embodiments of the present invention, even though a reduction in titer was observed as a result of very high expression levels of the recombinant proteins, their respective titer routinely approached 5×10⁷ pfu/ml, a level which is required for large scale production. Indeed, these two recombinant proteins have been efficiently produced in 293 suspension cultures in volumes of up to 5 liters, yielding approximately 45–50 mg of protein per $1 \times 10^9$ cells.

Since in Ad-infected cells the total amount of the late viral proteins are between 30–40% of total cellular proteins, the level of 15–20% of total cellular proteins being recombinant protein produced using the present invention, and at the expense of late viral proteins, indicates that near saturation level for this expression system has been reached. Further improvement in the efficiency of expression of the recombinant protein would likely result in the generation of recombinant Ad so crippled that they would not grow well enough to permit large scale production. Hence, the expression obtained with the preferred vectors of the present invention approaches the upper limit of the system when bearing scale-up considerations in mind.

The following examples are provided to illustrate rather than limit the scope of the present invention.

EXAMPLE 1

Cells and Viruses

The 293A (adherent) cells are derived from human kidney fibroblast transformed with Ad5 DNA, and express the E1A and E1B proteins constitutively. They were obtained from the ATCC and cultured in Dulbecco's modified Eagle's medium (DMEM; Gibco Laboratories), supplemented with 10% fetal bovine serum (FBS), glutamine and antibiotics. The 293S (suspension) derived from the 293A adapted to grow in suspension, were obtained from Dr. Michael Matthew (Cold Spring Harbor) and grown as spinner cultures in Joklik's modified medium (Sigma) supplemented with 2.5 g/L of glucose, 2.5 g/L of HEPES, 5% calf serum (CS) and antibiotics. Human Ad mutant Ad5/ΔE1ΔE3 (Gluzman et al., 1982, supra), was used as the parent virus in all the viral constructs, and recombinant Ad were propagated by infecting monolayer 293 cells as described previously (Massie et al., 1986, supra). AdRed-1, a helper-free Ad recombinant expressing the HSV-2 ribonucleotide large subunit R1 has been previously described (Huang et al., 1988, *Virology* 163:462–470). Large-scale production of Ad stocks was done by infecting exponentially growing 293S cells (0.5× 10⁶ cells/mL) at a MOI of 10–50 PFU/cell and harvesting the infected cells at 72 hours post-infection. The cell pellet was then resuspended in fresh Joklik's modified medium at a cell density of $1 \times 10^8$ cells/ml and virions were released by three to six cycles of freezing and thawing. Adenovirus titers were determined by plaque assays on 293A cells.

*Spodotera frugiperda* (Sf9) cells were obtained from ATCC and grown as spinner cultures in TNMFH medium supplemented with 10% FBS and 0.1% Pluronic F-68 as described (Caron et al., 1990, *Biotechnol. Bioeng.* 36:1133–1140). *Autographa californica* nuclear polyhedrosis virus (AcNPV), a baculovirus (Bac) used to construct Bac recombinants was propagated by infecting suspension Sf9 cultures as described previously (Caron et al., 1990, supra). Baculovirus titers were determined by plaque assay on monolayer cultures of Sf9 as detailed previously (Summers et al., 1987, *Texas Agricultural Experiment Station Reserach Bulletin no.* 1555).

Cell counting was performed using a hemacytometer, and viability was determined by trypan blue dye exclusion.

EXAMPLE 2

Construction of an Improved Transfer Vector

Figure 2:
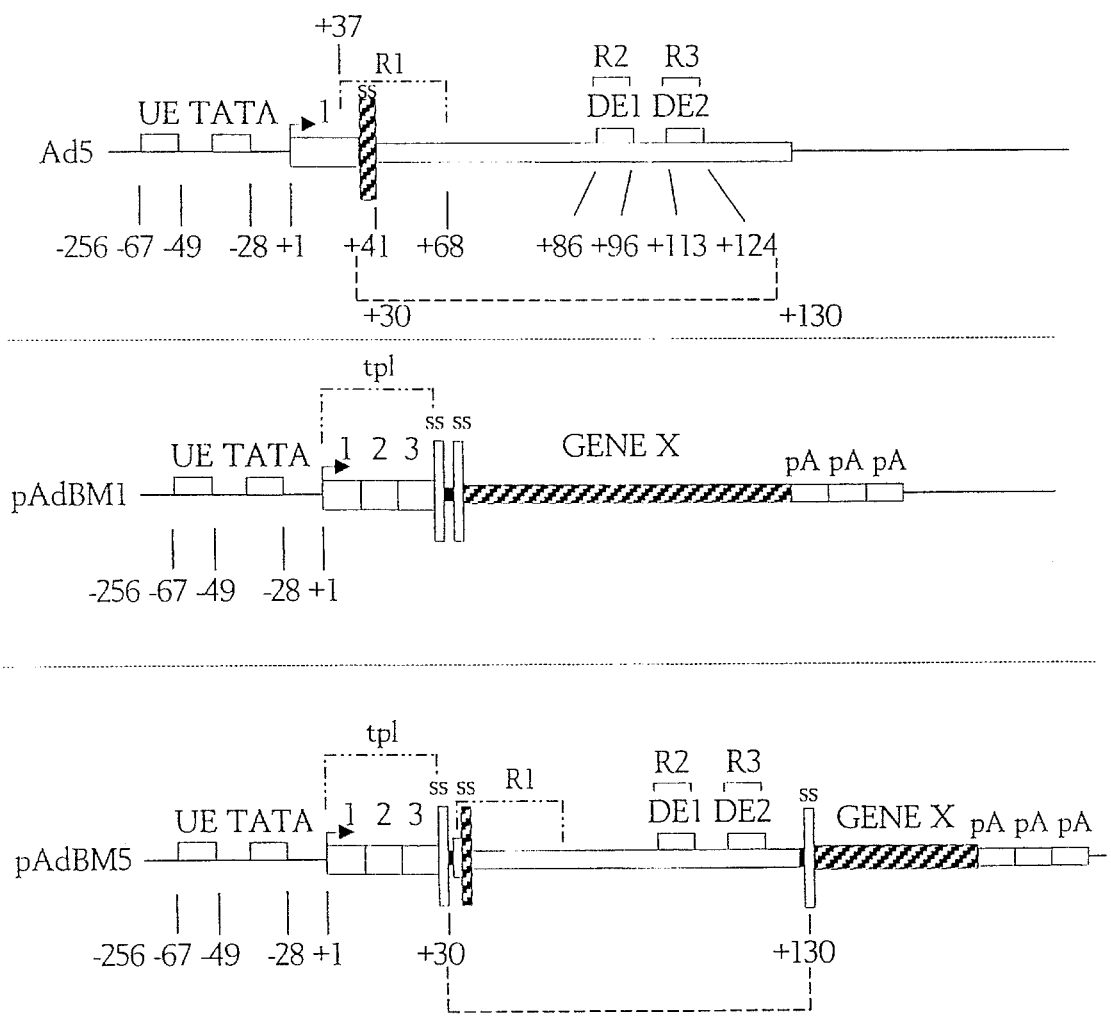
FIG. 2 shows diagrams of Ad5 endogenous MLP DNA fragment as found in its normal location in the genome, and ectopic MLP DNA fragments as found in Ad transfer vectors (diagrams are not drawn to scale). Symbols: (SS) splicing signal, (tpl) tripartite leader, (pA) polyadenylation signal.
Figure 4:
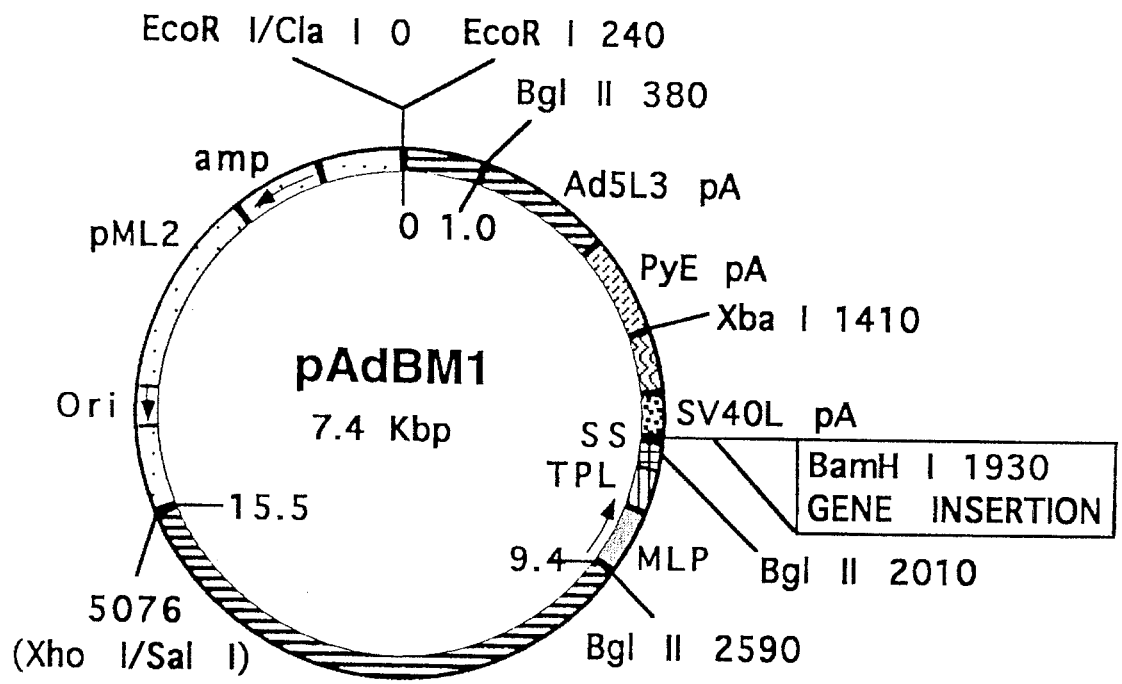
FIG. 4 is an illustration of the genetic maps of pAdBM1 and pAdBM5 transfer vectors. As shown, pAdBM5 was derived from pAdBM1 by successive cloning of BKV enhancer elements at Bgl II sites nucleotides 380 and 2590, and Ad2 MLP enhancer-like element at Bgl II site nucleotide 2010 on pAdBM1 map. The inner numbers on the vector refer to position map units (m.u.) on Ad5 genome (for symbols, see legend, FIG. 2). Briefly, pML2 is the *E. coli* replicon; the segments with dashed lines (0–1, and 9.4–15.5 m.u.) bracketing the expression cassette (between 1.0 and 9.4 m.u.) are Ad5 subgenomic portions involved in homologous recombination to generate Ad recombinant, as shown in FIG. 3, and in Ad replication.
Figure 4:
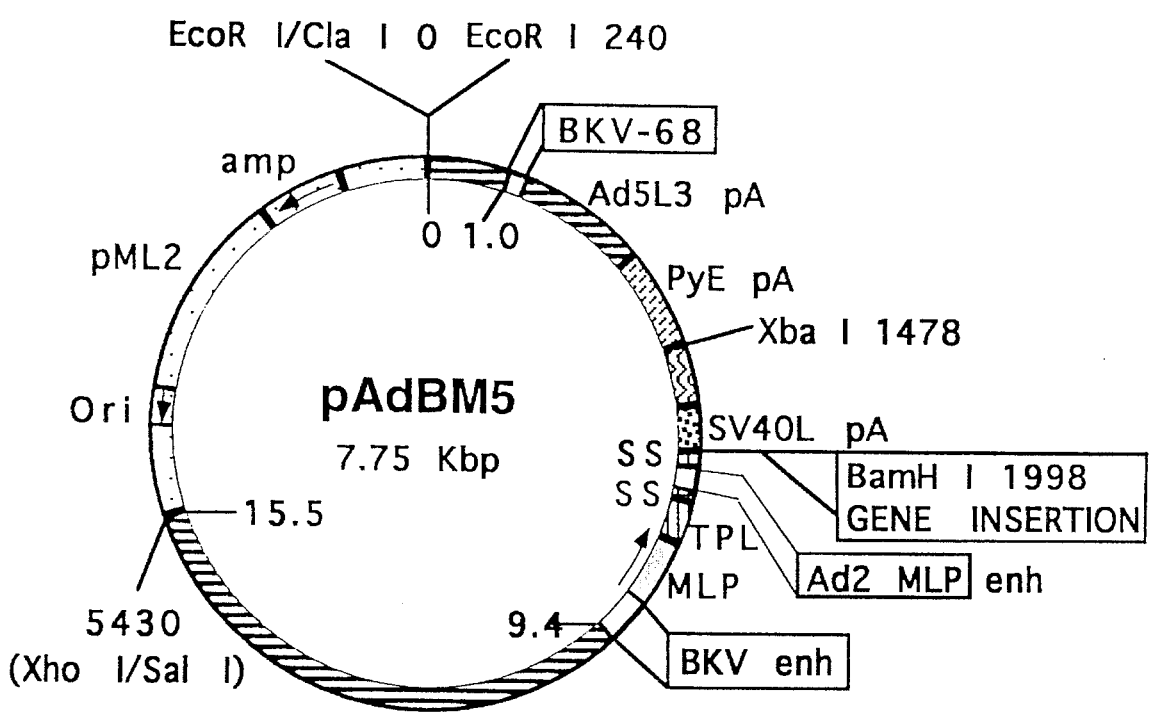

All recombinant DNA molecules were constructed by standard cloning and site-directed mutagenesis procedures and propagated in *E. coli* DH5. The transfer vector pAdBM5 was derived from pAdBM1 (Lamarche et al., 1990, supra) by sequentially subcloning three different synthetic oligonucleotides with compatible Bgl II ends as follows. Firstly, a double-stranded 73-mer oligonucleotide containing one copy of the 68 bp repeat of the BKV enhancer (Dunlop isolates described in Seif et al., 1979, *Cell* 18:963–977) was cloned at the Bgl II at map position 380 on pAdBM1; secondly, a double-stranded 198-mer oligonucleotide containing one copy of the entire BKV enhancer (Seif et al., 1979, supra) was cloned at the Bgl II at map position 2590 on pAdBM1; and finally a double-stranded 108-mer oligonucleotide containing the downstream late-phase-specific activating sequences of the Ad MLP (R1, R2, and R3), mapping between +30 and +130 relative to the transcription start site, was cloned at the Bgl II at map position 2010 on pAdBM1. The genetic maps of the parent plasmid pAdBM1 and the new plasmid derived therefrom, pAdBM5, are shown in FIG. 4. In summary, pAdBM5 was produced from pAdBM1 by inserting the BKV enhancer (SEQ ID NO:2) at position −256 relative to the MLP transcription start site; cis acting elements (R1, R2 and R3; SEQ ID NO:1)) were cloned into the intron lying between the third segment of the Ad tripartite leader and the BamH I cloning site. Thus, in pAdBM5 the cis-acting elements have been displaced by more than 200 bp further downstream relative to their position in the endogenous MLP (FIG. 2) where they are located within the intron between the first and second segment of the tripartite leader. It should also be emphasized that moving these cis-acting sequences downstream of the third segment of the tripartite leader also introduced, during the process, an additional 5' splice donor site.

EXAMPLE 3

Production of Recombinant Adenovirus 3.1 General Overview

Figure 3:
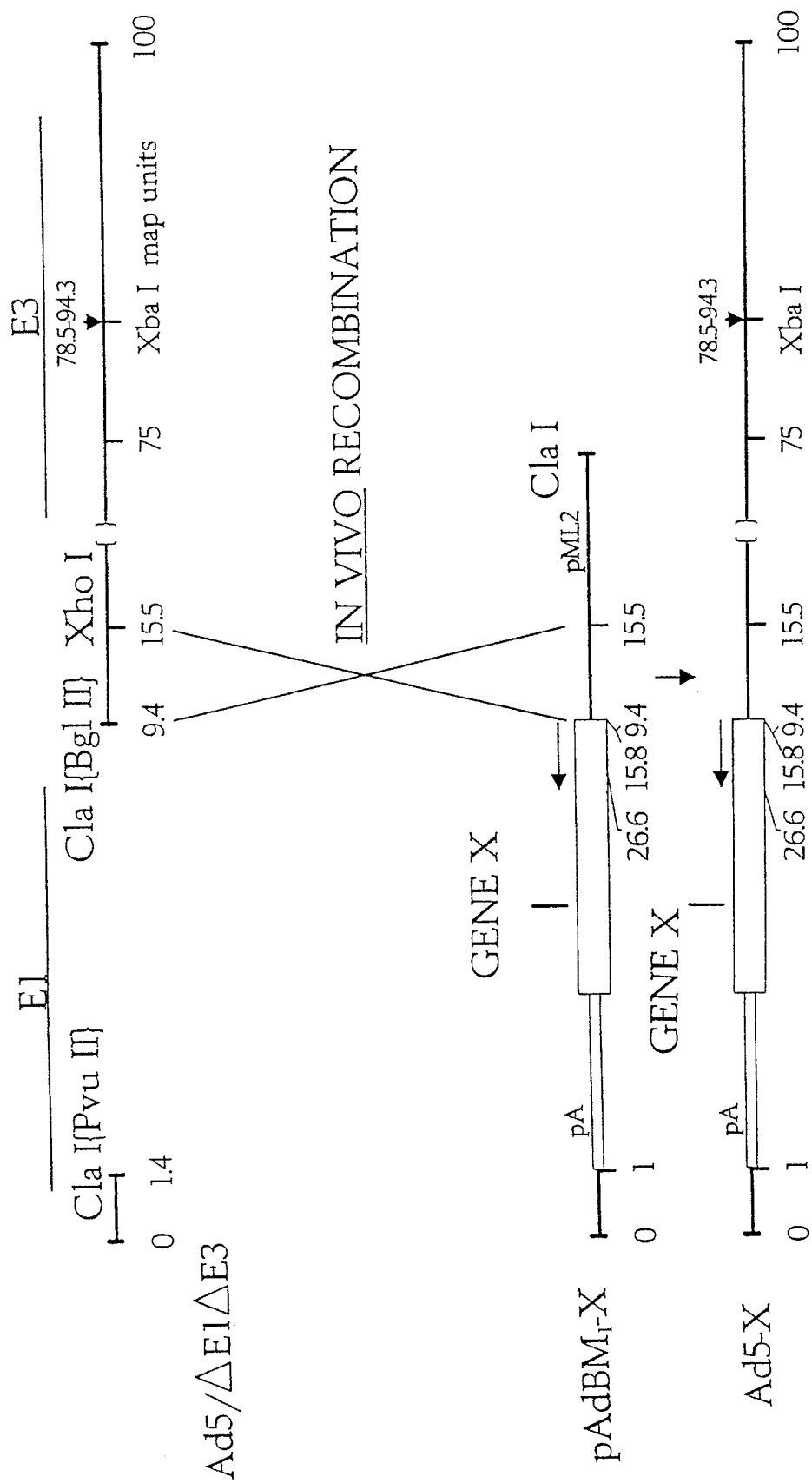
FIG. 3 is a diagram showing the production of recombinant Ad.

As a general overview, the coding region of the desired heterologous gene is first cloned in transfer vectors such as pAdBM1, or pAdBM5, at the unique BamH I cloning site, downstream of the strong Ad2 major late promoter. FIG. 3 demonstrates the production of recombinant adenovirus based on such a transfer vector. The resulting recombinant plasmid is then rescued into the genome of the adenovirus vector Ad5Δ&E1/ΔE3 by in vivo homologous recombination between overlapping sequences on the linearized plasmid and the large right-end fragment of the Ad5 genome, upon cotransfection of human 293 cells. This cell line constitutively expresses the Ad5 E1 gene products which are essential for the helper-free propagation of Ad5ΔE1/ΔE3 derived recombinants. Digestion of Ad5ΔE1/ΔE3 viral DNA with Cla I prior to transfection allows for obtention of recombinant adenovirus at a frequence of 5–20%.

3.2 Construction of HSV-2 R1 and R2 Recombinant Viruses

To illustrate this embodiment of the present invention, and to demonstrate that the inclusion of the cis-acting elements and creation of the additional 5' splice donor site improves the efficiency of the Ad transfer vectors, a series of Ad recombinants were constructed with pAdBM1 and pAdBM5 expression cassettes containing the HSV-2 R1 and R2 ribonucleotide reductase subunit genes.

Briefly, the cloning of HSV-2 R1 and R2 gene in pAdBM1 and pAdBM5 transfer vectors proceeded as follows. pAdBM1-R1 was constructed by cloning the BamH I fragment of the plasmid A392-B (kindly provided by Dr. Sylvia Bacchetti) encoding the HSV-2 R1 subunit into the BamH I site of pAdBM1. The initial plasmid A392-B was further modified to replace the (TCCATGG) motif at the R1 initiator codon by an optimal Kozak's consensus sequences (underlined) for efficient translation, by cloning a double-stranded 23-mer oligonucleotide (5'-CCATGGATCC[GCC]$_3$ ATGG-3'; SEQ ID NO:3) at the Bal I site. Insertion of the synthetic DNA restored the initiator ATG in frame and created a new BamH I site in adjacent upstream sequences. pAdBM5-R1 was then constructed by cloning the BamH I fragment of the modified A392-B plasmid at the BamH I site of pAdBM5. pAdBM5-R2 was constructed by cloning the Bgl II-Bcl I fragment encoding the HSV-2 R2 subunit from pSVRR2$^{HSV}$ at the BamH I site of pAdBM5 as was previously described for pAdBM1 (Lamarche et al., 1990, supra).

The generation of Ad5BM1-R2 recombinant (formerly named Ad5BM1-RR2$^{HSV}$) has been described previously (Lamarche et al., 1990, supra). The other recombinant Ad, Ad5BM1-R1, Ad5BM5-R1, and Ad5BM5-R2 were constructed with the appropriate plasmids essentially in the same way with modifications (van Drunen Littel-van den Hurk et al., 1993, *Vaccine* 11:25–35). Briefly, the Ad transfer vectors pAdBM1-R1, pAdBM5-R1 and pAdBM5-R2 were linearized at the unique Cla I site by digesting 20–50 µg of plasmid DNA with Cla I. The linearized plasmid is then extracted once with buffer-saturated phenol and chloroform/isoamyl alcohol (24:1), precipitated with 2.4 volumes of ethanol, and resuspended in 50 µl of sterile TE 1/10. The concentration of the linearized plasmid is then estimated in an agarose gel.

Ad5ΔE1/ΔE3 viral DNA is prepared by infecting 293 cells with Ad5ΔE1/ΔE3 at a m.o.i. of 5–10; harvesting the cells 40–48 hours post-infection; washing the harvested cells twice with cold PBS; and resuspending the cells in 10 mM Tris pH 7.9 (2 volumes per volume of cell pellet). The cell pellet is then freeze-thawed 3 times to release intracellular viral particles, and extracted with 1,1,2-trichlorotrifluoroethane (freon) as follows: (all steps on ice). Mix an equal volume of cell suspension and freon and blend in an omnimixer at full speed for 2 minutes. Spin mixture at 2K for 15 minutes; collect top phase (aqueous); and reextract the freon phase twice with the same volume of buffer (10 mM Tris pH 7.9).

The virions are purified through 2 consecutive CsCl gradients. A step gradient is performed by pouring 8 ml of CsCl 1.4 (53 gr+87 ml of 10 mM Tris pH 7.9) into SW 27 cellulose nitrate tubes, and then very gently on top pour 56 ml of CsCl 1.2 (26.8 gr+92 ml of 10 mM Tris pH 7.9). The aqueous phase containing the virions is then loaded on top of the discontinuous gradient (up to 22 ml/tube). The tubes are then centrifuged at 23K for 90 minutes at 0° C. The virus band is then collected by side puncture of the tubes. The band is diluted ½ in 50 mM Tris pH 7.5, 1 mM EDTA.

A continuous gradient is then performed by using a gradient maker, to pour a continuous CsCl gradient in SW27 cellulose nitrate tubes using 12 ml of CsCl 1.4 and 14 ml of CsCl 1.2. The diluted virus suspension (8–10 ml) is then loaded very slowly on top of the gradient. The tubes are then centrifuged at 23K for 16–20 hours at 0° C. The virus band is then collected by side puncture, and dialyzed against 100 volumes of 10 mM Tris pH 7.9, 1 mM EDTA (3 changes), and finally against 100 mM Tris pH 8.5 1 mM EDTA.

Viral DNA is purified from virions by incubating the virus at 37° C. for 2 hours with self-digested pronase at a final concentration of 1 mg/ml and SDS 0.5%. NaCl is added to a final concentration of 100 mM, and the digest is then extracted twice with buffer-saturated phenol, once with chloroform/isoamyl alcohol (24:1), and then precipitated with 2.5 volumes of ethanol. Ad5ΔE1/ΔE3 viral DNA is then digested with an excess of Cla I (map unit 10) to minimize the fraction of undigested viral genomes since they represent the background noise in the screening of recombinant viruses. Typically, 5 units of ClaI/µg of viral DNA are added for 3 consecutive incubations of 1 hour at 37° C. An aliquot of the preparative digestion is further digested with HindIII and analyzed by comparing the restriction pattern with the pattern obtained upon digestion with HindIII alone. If the Cla I digestion is incomplete, the preceding step is repeated. Cla I-cut Ad5ΔE1/ΔE3 DNA is then extracted once with buffer-saturated phenol and chloroform/isoamyl alcohol (24:1), precipitated with 2.5 volumes of ethanol and resuspended in 50 µl of sterile TE 1/10. The concentration is estimated in an agarose gel.

Linearized Ad transfer vectors (pAd5BM1-R1, pAd5BM1-R2, pAdBM5-R1, and pAdBM5-R2) were rescued into the genome of Ad5/ΔE1ΔE3 by in vivo homologous recombination between overlapping sequences on the transfer plasmid and the large right-end fragment of Ad5/ΔE1ΔE3 genome, upon cotransfection of 293A cells. Digestion of Ad5/ΔE1ΔE3 viral DNA with Cla I prior to transfection allowed for obtention of recombinant Ad at a frequency of 5 to 50%. 293 cells were transfected to generate Ad5 recombinant by first plating the cells in 60 mm-diameter dishes at 1.0×10$^6$ cells/ml one day prior to transfection (in DMEM+10% FBS+antibiotics). Transfer plasmid (5 µg linearized with Cla I) containing the gene to be expressed (HSV-2 R1 or R2) is mixed with 5 µg of Cla I-cut Ad5ΔE1/ΔE3 viral DNA and transfected onto subconfluent 293 cells using the standard calcium phosphate technique. As a control for the transfection, 1 µg of Ad5ΔE1/ΔE3 viral DNA+9 µg of carrier DNA is also transfected. This should yield more than 100 plaques. After overnight incubation, the DNA-calcium phosphate co-precipitate is removed, the cells monolayer washed once with EGTA 1 mM in PBS and twice with PBS and splitted into 3×60 mm-diameter dishes. After 4–6 hours, the medium is removed and the cell monolayers are overlayed with 1% agarose (mix agarose 5% 1:5 with DMEM+10% FBS+ antibiotics).

Viral plaques (usually 20–60) that appear between days 5 and 15 post-transfection are picked (as agarose plugs) and grown on 293 cells into 24 wells plates (5×10$^4$ cells/well). (Complete CPE is obtained in 3–7 days). The amplified plaques are tested either for HSV- R1 or R2 expression by Western blotting using rabbit peptide serum. At least two positive independent plaque isolates were further purified by two consecutive rounds of plaque assays, and viral stocks were prepared as described above.

Ad5 recombinants may be further screened by isolating viral DNA. A lysate for each individual plaque is made by extracting each plaque with 10 µl of 10% SDS and 10 ml of pronase (20 mg/ml) with incubation at 37° C. for 2 hours. The DNA is then denatured by adding 40 µl of 1M NaOH (incubated at R.T. for ~10 min.) and neutralized by adding sequentially 40 µl of 1M Tris pH 7.5 and 40 µl of 1M HCl. The DNA is finally put on a hybridization membrane using a dot blot apparatus and screen with the appropriate probe following standard procedures.

EXAMPLE 4

Characterization of Recombinant Adenovirus Expression

The production of HSV-2 R1 and R2 recombinant proteins was done by infecting suspension cultures with the appropriate recombinant viruses. Ad infections were performed by mixing exponentially growing 293S cells (0.5× $10^6$ cells/mL) with a viral inoculum corresponding to a MOI of 25–50 PFU/cell and harvesting the infected cells usually at 48 hours post-infection. Alternatively, spinner cultures (3 to 6 L) of 293S between 1.5 and 2.5×$10^6$ cells/ml were pelleted, resuspended at 1×$10^7$ cells/ml, incubated with a viral inoculum corresponding to a MOI of 25–50 PFU/cell for 2 hours, diluted to 2×$10^6$ cells/ml with fresh Joklik's medium, and incubated at 37° C. Twenty four hours post-infection, the medium was replaced. Again, the infected cells were harvested 48 hours post-infection, washed twice with ice-cold PBS, pelleted, resuspended in ice-cold buffer A (50 mM Hepes pH7.6, 2 mM DTT) and frozen at –80° C.

Like Ad5BM1-R2, the genomes of the recombinants constructed according to Example 3 are approximately the same size as wild-type Ad5, and are stable after at least ten rounds of amplification; i.e. sufficient to produce large stocks of viruses or recombinant proteins. Ad5BM1-R2 and Ad5BM1-R1 grew routinely to titers slightly lower than that of their parental virus, Ad5/ΔE1ΔE3, whereas Ad5BM5-R2 and Ad5BM5-R1 grew to titers 5 to 10 times lower and produced smaller plaques. As previously reported, the synthesis of recombinant R2 in 293 cells infected with Ad5BM1-R2 follows a pattern similar to that of the Ad late proteins, which synthesis begins 12 hours post-infection, rapidly increases by 16 hours, and remains elevated until 30 hours post-infection (Lamarche et al., 1990, supra). The time course production of recombinant R2 production by Ad5BM5-R2-infected 293 cells was analyzed by preparing cell extracts from infected cells at various time points post-infection and subjecting them to SDS-PAGE. Cell extracts were prepared from infected cells at various time post-infection either directly on petri dishes or from aliquots of suspension cultures containing between 1 and 2×$10^6$ cells/ml. Briefly, cells were washed twice with PBS, lyzed in 100 μL/mL of extraction buffer (80 mM tris pH6.8, 2% SDS, 10% glycerol), and frozen at –20° C. For gel electrophoresis, samples were thawed, passed several times through a syringe needle or sonicated to shear the DNA, and boiled 5 minutes in standard sample buffer. Protein concentration was determined in the cell extract using a colorimetric assay with BSA as standard. SDS-PAGE and Western blotting was performed as described previously (Lamarche et al., 1990, supra). Quantification of recombinant R1 and R2 in cell extracts was done by densitometry scanning of Coomassie blue-stained gels or immunoblots using >95% pure R1 or R2 proteins as standards.

Figure 5B:
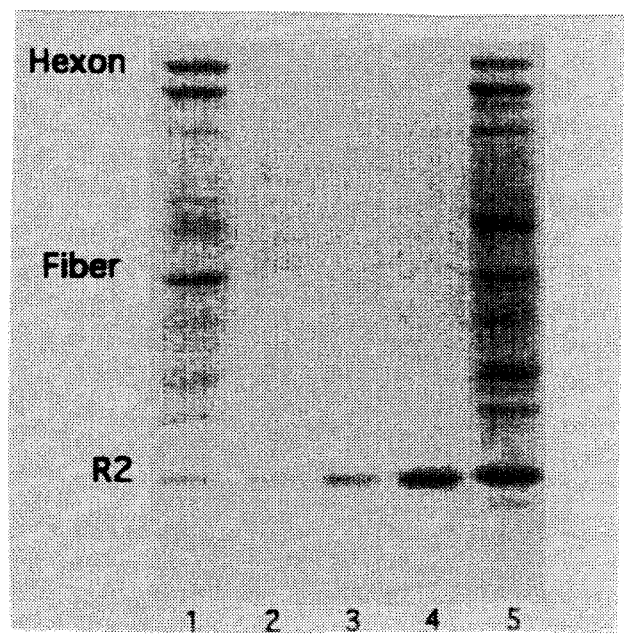
FIG. 5B shows quantification of R2—lane 1: 30 μg of Ad5BM1-R2-infected 293 cell extract; lanes 2–4: 1, 2, and 4 μg respectively, of >95% pure R2; and lane 5: 30 μg of Ad5BM5-R2-infected 293 cell extract.
Figure 5A:
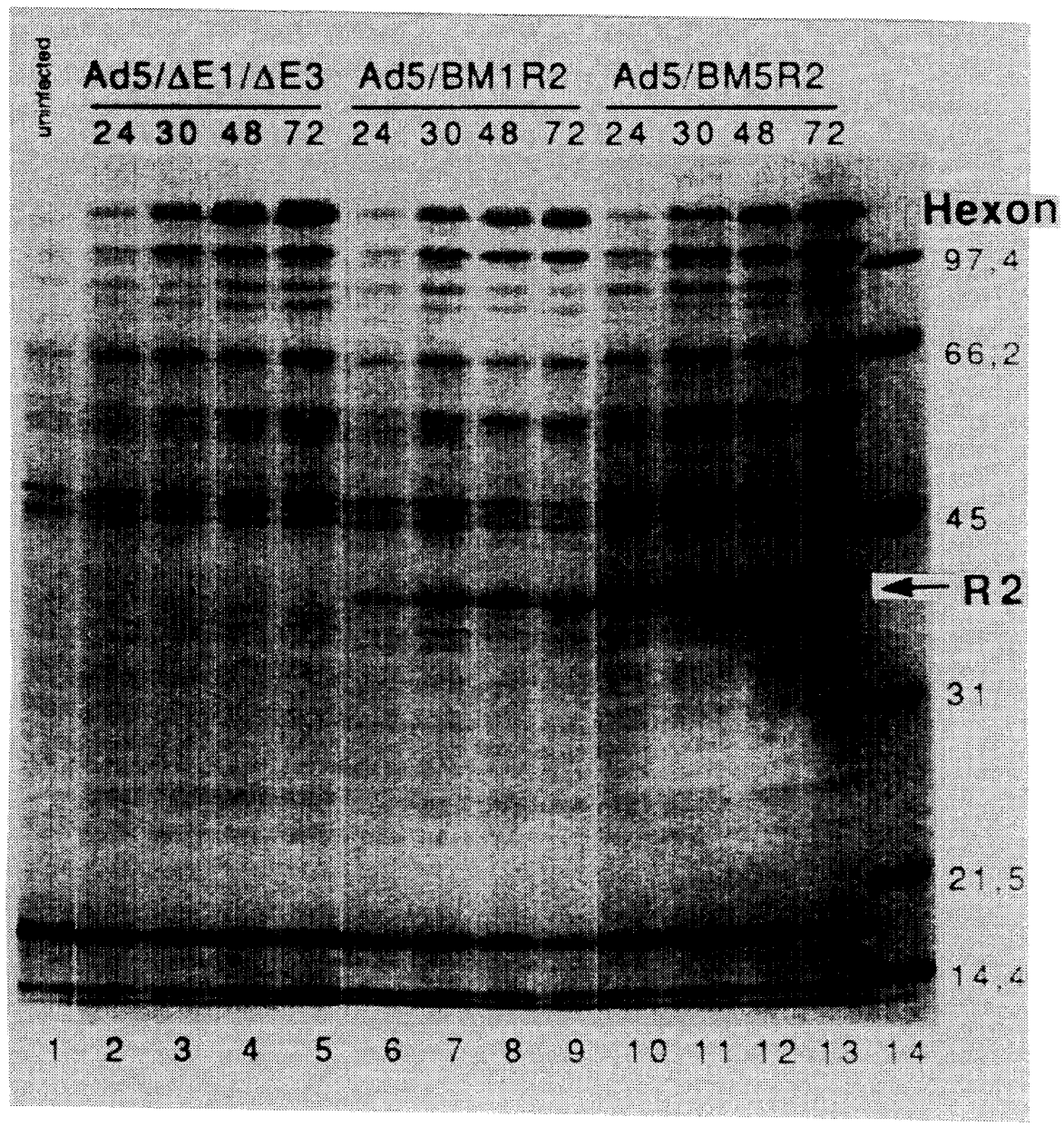
FIG. 5A shows equal amounts of total proteins produced in 293 cells infected with Ad5/ΔE1ΔE3 (lanes 2–5), Ad5BM1-R2 (lanes 6– 9), and Ad5BM5-R2 (lanes 10–13).

As shown in FIG. 5A, the R2 protein synthesized by Ad5BM5-R2-infected 293 cells accumulated during the late phase of infection at a rate similar to that observed in Ad5BM1-R2-infected 293 cells, but at significantly higher levels. Indeed, in Ad5BM5-R2-infected cells, R2 was clearly the most abundant protein by 30 hours post-infection and its level remained constant thereafter. Compared to the parental virus, Ad5/ΔE1Δ3, the relative amount of the hexon was more reduced with Ad5BM5-R2 than with Ad5BM1-R2 (FIG. 5A). Concomitant with this reduction in the level of the hexon, was observed a proportional reduction in the titers of the respective recombinant Ad. This suggests that the synthesis of the recombinant protein takes place at the expense of the Ad abundant late proteins and that, given the magnitude of reduction in the titer, the expression level obtained is probably very close to the upper limit of the system.

In order to precisely quantitate the amount of R2 produced in Ad5BM5-R2 and Ad5BM1-R2-infected 293 cells, the relative intensity of the R2 band in a Coomassie blue stained gel was measured using computer-assisted image analysis and purified R2 as an internal standard. For example, as shown in FIG. 5B, 30 μg of total protein extract has been loaded in lanes 1 and 5 next to 1, 2, and 4 μg of R2 (lanes 2–4), and the amount of R2 produced was estimated at 4% and 13% of total cellular proteins respectively for Ad5BM1-R2 and Ad5BM5-R2. Similar quantification from several infections done under optimal conditions yielded levels within the range of 4–5% for Ad5BM1-R2 and 11–15% for Ad5BM5-R2. Thus, Ad5BM5-R2-infected 293 cells produced about 3-fold more R2 protein than Ad5BM1-R2-infected 293 cells.

Figure 6A:
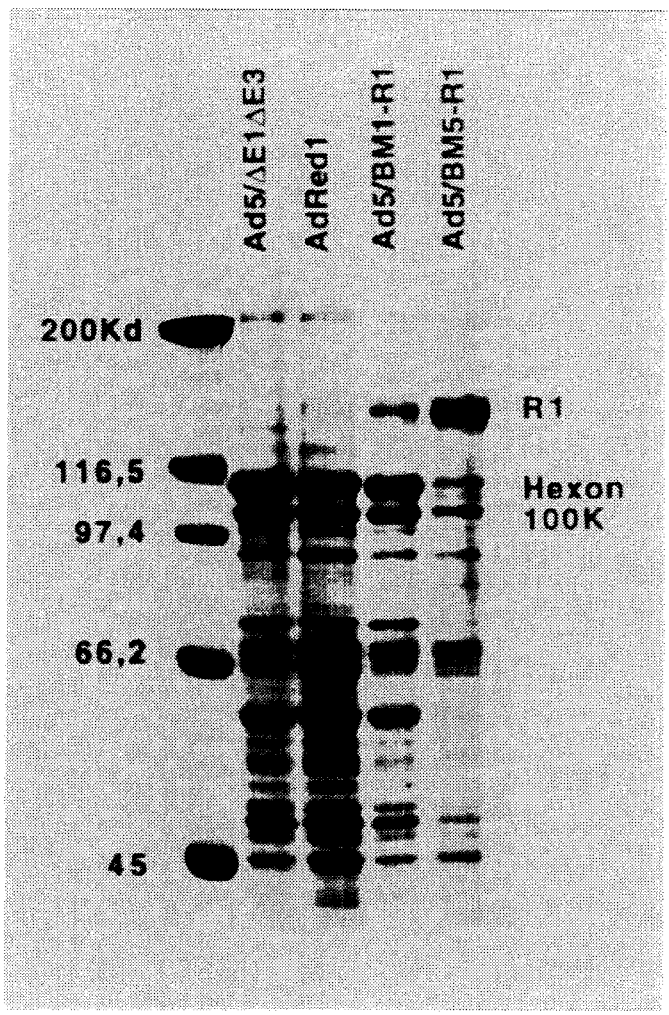
FIG. 6A is a stained SDS-PAGE gel showing equal amounts of total proteins produced in 293 cells infected with Ad5/ΔE1ΔE3 (lane 1), AdRed-1 (lane 2), Ad5BM1-R1 (lane 3), and Ad5BM5-R1 (lane 4).

To determine whether the increased expression of recombinant protein with pAdBM5 vector was unique to HSV-2 R2, the relative expression efficiency of pAdBM1 and pAdBM5 derived recombinants encoding another gene, the HSV-2 R1, was compared. The levels of recombinant R1 expression were compared in Ad5BM1-R1 and Ad5BM5-R1-infected 293 cells at 48 hours post-infection as described above for recombinant R2. As shown in FIG. 6A, the expression level of HSV-2 R1 was increased about 4-fold in Ad5BM5-R1-infected 293 cells (lane 4) compared to Ad5BM1-R1-infected 293 cells (lane 3) under optimal conditions of infection. Quantification using purified R1 protein as a standard yielded levels of expression within the range of 4–5% of total cellular proteins for Ad5BM1-R1 and 12–20% for Ad5BM5-R1.

Figure 6B:
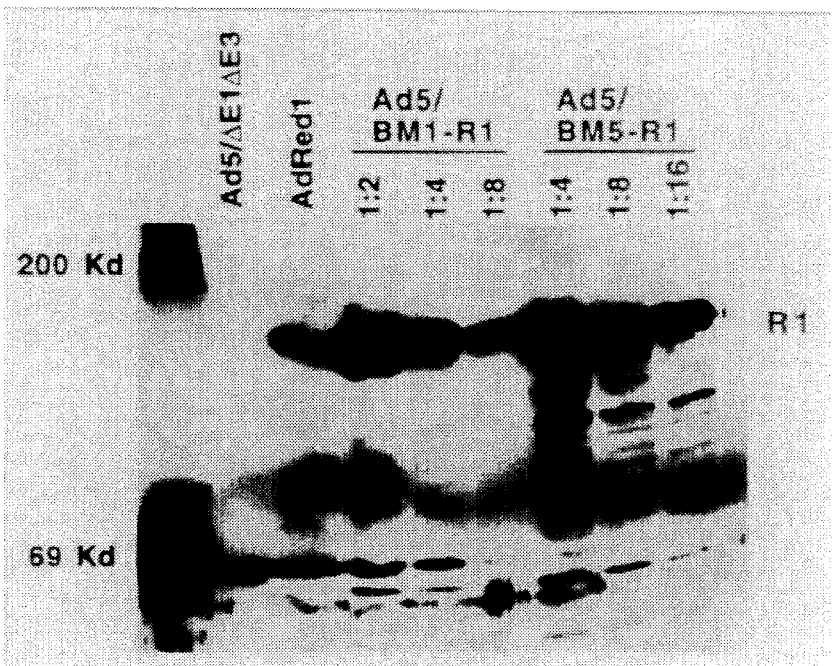
FIG. 6B is a Western blot of dilutions indicated of cellular extracts—lane 1: Ad5/ΔE1ΔE3; lane 2: AdRed-1; lanes 3–5: Ad5BM1-R 1; and lanes 6–8: Ad5BM5-R1.

The level of expression of HSV-2 R1 obtained with Ad5BM1-R1 was also compared to that obtained with the previously published recombinant, AdRed-1, which uses a similar MLP-based vector to express the HSV-2 R1 protein (Huang et al., 1988, supra). As shown in FIG. 6A, the expression of R1 protein by AdRed-1 (lane 2) is not detectable on Coomassie blue stained gel but only by Western blotting (FIG. 6B, lane 2). Quantification of the immunoblots (FIG. 6B) indicated that the amount of recombinant R1 produced by AdRed-1 (lane 2) was more than 8-fold lower than Ad5BM1-R1 (lanes 3–5). The main difference between these two constructs is the inclusion of three polyadenylation sites in Ad5BM1-R1. This result emphasized the importance of efficient polyadenylation for high-level expression of recombinant protein in MLP-based vectors.

Figure 8A:
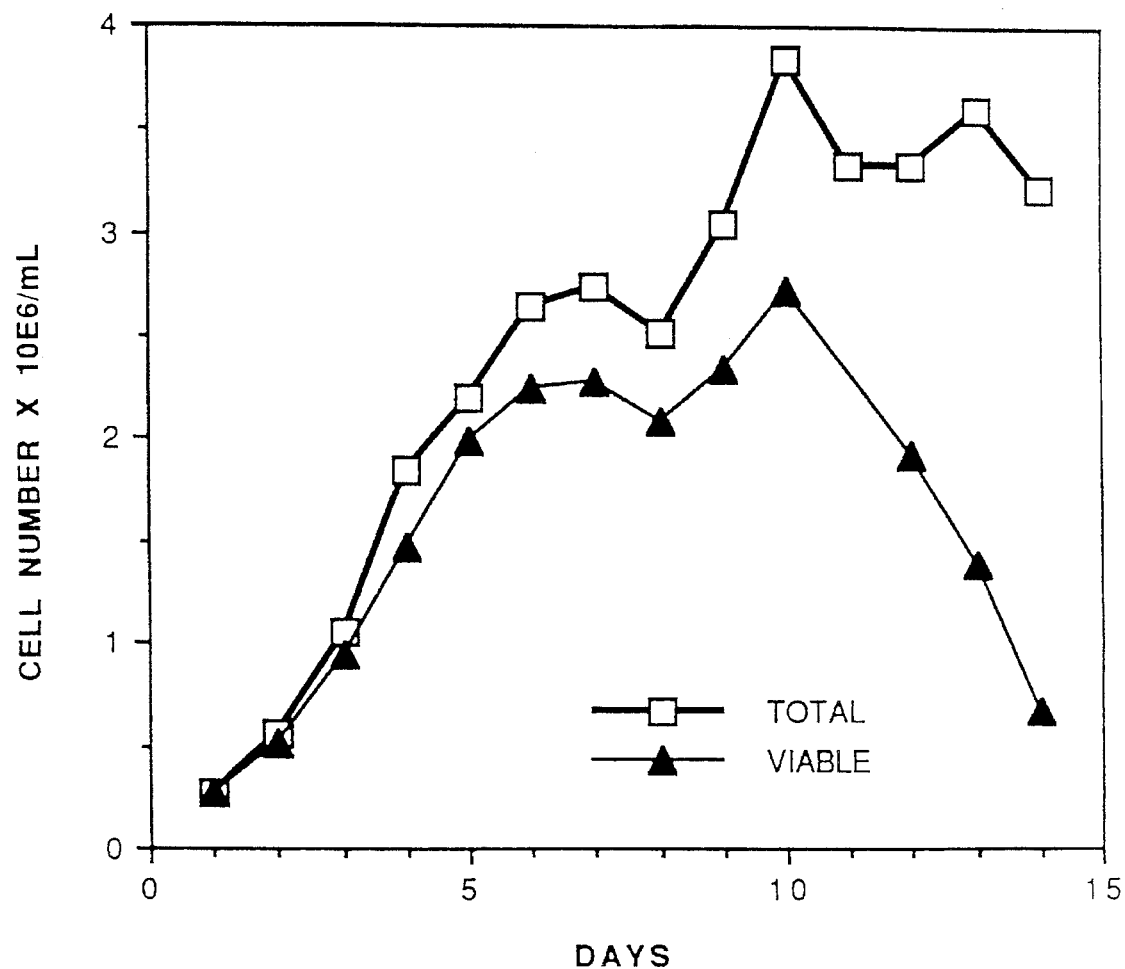
FIG. 8A is a typical growth curve of 293S cells in 100 ml spinner flask culture.

An important feature of expression systems for high level production of recombinant proteins, is the ability to easily grow the expression vector host cell lines in large volumes. Suspension cultures are the overwhelming choice for large-scale production processes with animal cells. Recently obtained was a 293 cell line (293S, from CSH Laboratory) that has been successfully adapted to grow in suspension in Joklik's medium (without $Ca^{++}$). Although the 293S cells tend to form aggregates when grown in suspension culture, they are easy to culture since they can be diluted as low as 1×$10^4$ cells/ml, and routinely reach more than 2×$10^6$ viable cells/mL in a few days (FIG. 8A).

Figure 8B:
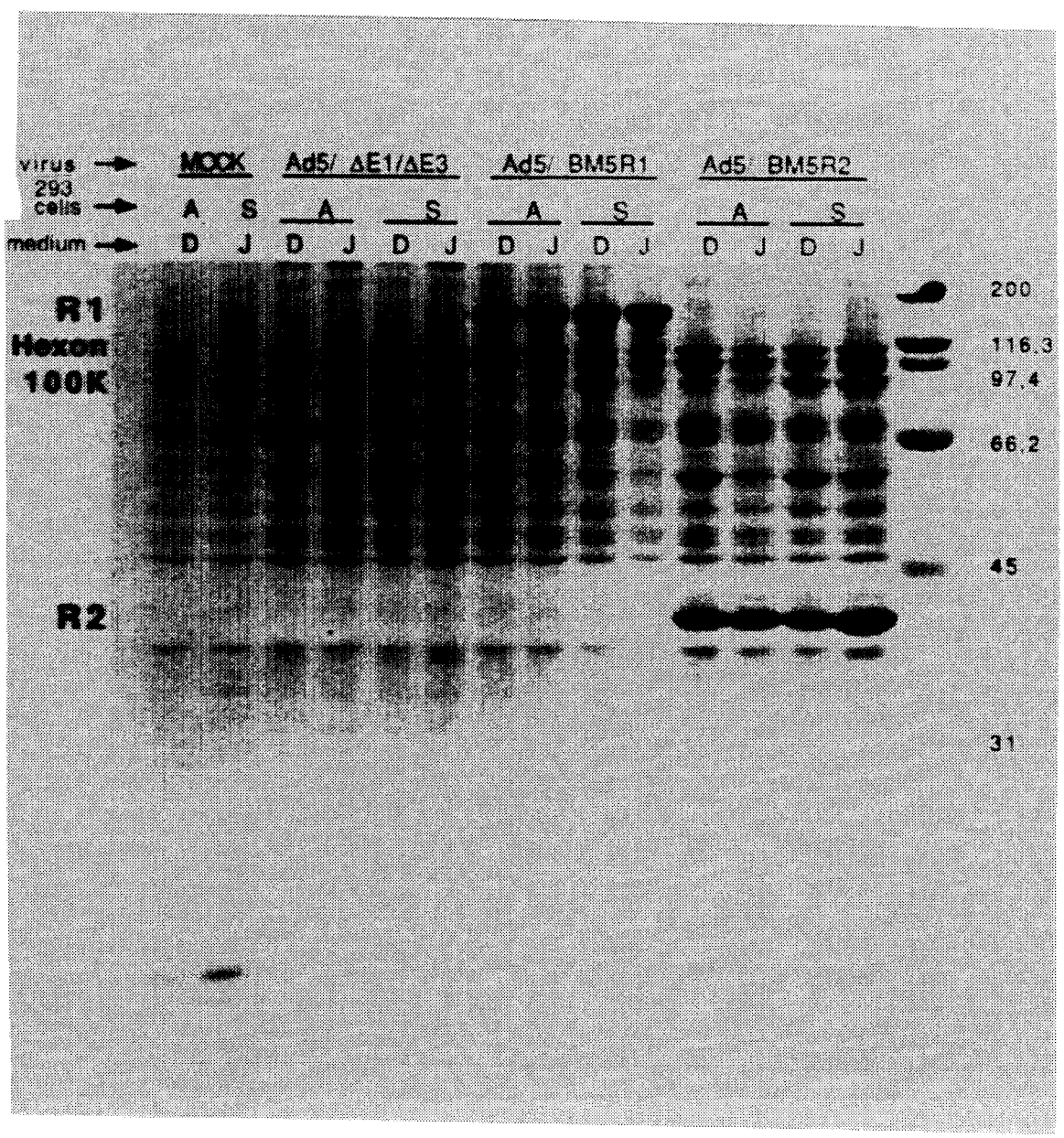
FIG. 8B is a stained SDS-PAGE gel of total proteins produced either in 293A (adherent) or 293S (suspension) cells infected with Ad5/ΔE1ΔE3; Ad5BM5-R1; or Ad5BM5-R2. Also indicated are molecular weight markers, and the position of R1, hexon, 100K and R2 proteins.

We have compared the production potential of 293S and to 293A (adherent) cells grown in monolayer culture with either DMEM+10% FBS or Joklik+5% CS. As shown in FIG. 8B, under optimal conditions of infection, no difference could be found with either cell line or media for the production of Ad late proteins or recombinant R1 and R2. It can also be appreciated that both recombinant R1 and R2 protein, produced using pAdBM5-derived recombinant Ad, clearly represent the most abundant protein in the cell extracts (FIG. 8B). Spinner cultures of 293S can therefore be used, under the appropriate culture conditions, as detailed in Experimental Protocol, to produce virus stocks and large amounts of recombinant R1 and R2 with the Ad expression system of the present invention.

EXAMPLE 5

Comparison of Ad and Bac (Baculovirus) Expression Systems for the Production, Purification, and Biological Activity of Recombinant Proteins Since the Bac expression vector systems is a very efficient system for high level production of recombinant proteins, the efficiency of production of HSV-2 R1 and R2 subunits was compared between the Bac expression system, and the Ad expression system of the present invention. Using the best Bac transfer vectors, the HSV-2 R1 and R2 genes placed under the control of the strong polyhedrin promoter and inserted into the genome of AcNPV to generate Bac-R1 and Bac-R2 respectively. For expression in Bac, the same BamH I fragment encoding the HSV-2 R1 subunit that was cloned in pAdBM1, was blunt-end ligated into the Nhe I cloning site of the transfer vector pJVETL to produce pJVETL-R1 (Richardson et al., 1992, *Intervirol.* 34:213–227). As well, the same Bgl II-Bcl I fragment encoding the HSV-2 R2 that was cloned in both Ad vectors, was cloned at the BamH I site of the transfer vector pac3731 to produce pAc3731-R2. pac3731 is a derivative of pac373 (Summers et al., 1987, supra) in which the missing 8 nucleotides from the polyhedrin leader were added while deleting 10 nucleotides derived from the polylinker used to introduce the BamH I cloning site pac373.

The Bac-R2 recombinant was generated from pAc3731-R2 using the standard procedure detailed in Summers and Smith (1987, supra). The Bac-R1 recombinant was generated from pJVETL-R1 following the same procedure improved by the visual screening of blue recombinant plaques as described previously (Vialard et al., 1990, *J. Virol.* 64:37–50). Bac infections of Sf9 cells were done as detailed previously (Caron et al., 1990, supra). Briefly, Sf9 cells were grown in 4 L bioreactors and infected with recombinant Bac with a MOI of 10 PFU/cell when the culture had reached typically between 1.5 and $2 \times 10^6$ cells/ml. Cells were harvested 48 to 72 hours post-infection and proteins extracts were prepared as described in Example 4 for Ad-infected 293S cells.

When the level of expression of recombinant R2 was examined in Sf9 cells infected by two different plaque isolates of Bac-R2, it was found to be lower than in Ad5BM1-R2 infected 293 cells. In fact, the R2 protein band from extracts of Bac-R2-infected Sf9 cells, resolved by SDS-PAGE, was barely detectable by Coomassie blue staining, and had to be quantitated by immunoblotting. Its level was estimated to be roughly 2-fold lower than Ad recombinant R2 produced in Ad5BM1-R2 infected 293 cells, which corresponded to 2% of total cellular proteins. This was surprising since the Bac transfer vector used to construct Bac-R2 was similar to the optimized vectors pAcYM1 and pAcRp23, that was used to express the bovine rotavirus VP6 protein at a level approaching the level of polyhedrin; i.e, approximately 20% of total cellular proteins (Caron et al., 1990, supra). To exclude the possibility that the Bac-R2 clones were not completely pure, or that bad plaque isolates may have been selected in the initial screening, (a situation which could, in both cases, explain the relatively low level of Bac recombinant R2), additional rounds of plaque purification were performed on these two clones and on another independent plaque isolate that was picked. The level of expression of these three independent stocks of Bac-R2 was estimated to be similar to the value obtained previously, with amounts within the range of 1.5–3% of total cellular proteins under optimal conditions of infection.

In order to evaluate more precisely the yield of expression of recombinant R2 produced by the Bac system compared to the Ad system, the R2 protein was purified from several liters of suspension cultures of either 293S infected cells (cultured according to Example 4) or Sf9 cells (cultured according to methods herein).

The purification of the R2 subunit was accomplished following the three step method of Lankinen et al. (1991, *J. Gen. Virol.* 72:1383–1392) with modifications. Briefly, the first step of purification consists of salt precipitations of cellular extracts. Streptomycin sulfate was added to the crude cellular extract to a final concentration of 1%; the mixture was stirred for 1 hour; and the suspension was centrifuged at 12,000g for 20 minutes to remove precipitated nucleic acids. The resulting supernatant was precipitated with ammonium sulfate (25% saturation); and the ammonium sulfate precipitate (containing the bulk of R2 protein) was dialyzed twice against buffer B (20 mM BisTris-HCl pH 5.8, 10% glycerol). The second step of purification consists of anion exchange chromatography by loading the dialyzed supernatant on an anion exchange column and eluting R2 protein with a gradient of KCl. The third step consisted of the determination of R2 protein concentration by the Coomassie blue method (Bradford, 1976, *Analytical Biochem.* 72:248–254); and degree of purity (>95%) by analyzing the amino acid content.

Figure 7:
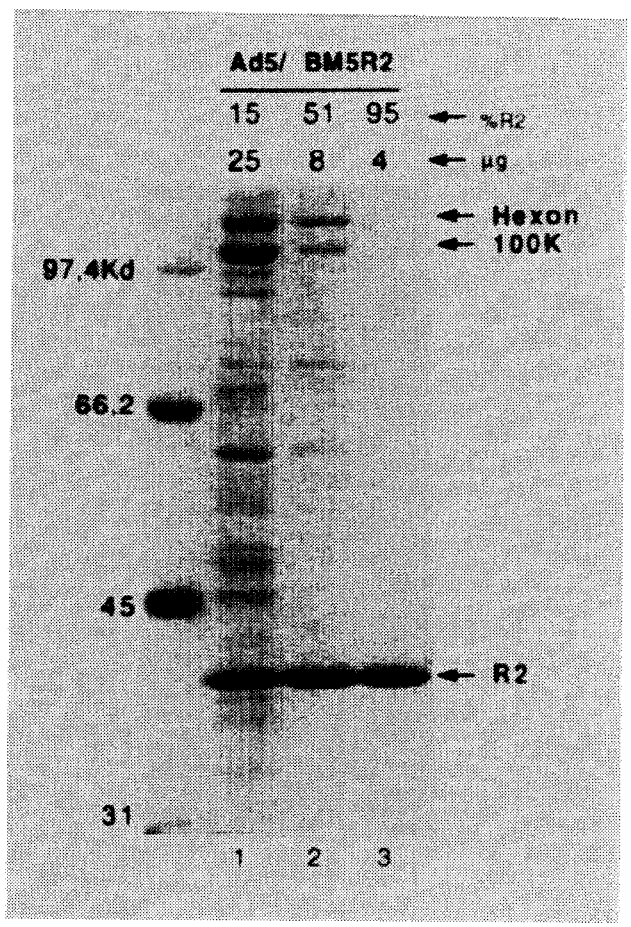
FIG. 7 is a stained SDS-PAGE gel showing protein extracts of recombinant R2, from 293 cells infected with Ad5BM5-R2, from different purification steps. Also indicated are molecular weight markers and the position of hexon, 100K, and R2 proteins.

The results of these purification experiments are summarized in Table 1. Because of its very high abundance in Ad5BM5-R2 infected 293 cells, the recombinant R2 can be readily purified to >95% (FIG. 7), using the method described herein. By contrast, the lower abundance of recombinant R2 in Bac-R2-infected Sf9 cells resulted in a degree of purity of only 36%, using the same purification protocol. The R2 protein purified from Ad5BM1-R2 infected 293 cells, yielded an intermediate degree of purity, approximately 52%.

At the beginning and the end of the purification, the protein extract was analyzed by SDS-PAGE and the activity of recombinant R2 was measured with an excess of HSV-2 R1. For measurement of ribonucleotide reductase activity in crude extracts, a fraction of the 12,000g supernatant was centrifuged through a Sephadex G-25 column to remove inhibitory molecules. Specific activity of recombinant R2 was determined by adding excess amounts of partially purified recombinant R1 produced by Ad5BM5-R1-infected 293 cells (specific activity 3 U/mg) to limiting amounts of R2 protein. Specific activity of recombinant R1 was determined by adding excess amounts of HSV-2 R2 protein produced in *E. coli* with the pET-R2 vector (specific activity 70 U/mg) to limiting amounts of R1 protein. Ribonucleotide reductase activity was assayed by monitoring the reduction of [$^3$H]-CDP as previously reported (Cohen et al., 1985, *J. Gen. Virol.* 66:733– 745). The standard reaction mixture contained 50 mM Hepes pH 7.8, 4 mM NaF, 50 µM CDP, and 0.25 µCi of [$^3$H]-CDP in a final volume of 60 µl. One unit of ribonucleotide reductase was defined as the amount of enzyme generating 1 nmol of dCDP/minute.

As shown in Table 1, the specific activity of recombinant R2 was essentially identical with either expression vectors, and it was indistinguishable from the specific activity of authentic R2 produced in HSV-2-infected BHK cells as previously reported (Lamarche et al., 1990, supra).

TABLE 1

|  | Ad5BM1-R2 | Ad5BM5-R2 | Bac-R2 | HSV-2 |
|---|---|---|---|---|
| Expression level (%) | 4 | 15 | 2 | 0.5 |
| Degree of purity (%) | 52 | >95 | 36 | not determined |
| Specific activity* | 6.6 | 27 | 3.4 | 0.8 |
| Specific activity** | 165 | 179 | 170 | 163 |
| Yield*** | 12 | 45 | 7 | n.d. |

*(U/mg total)
**(U/mg of R2)
***(mg of R2/$10^9$ infected cells)

The level of expression of R1 in the different systems was analyzed by purifying recombinant R1. Purification of recombinant R1 was similar to that of recombinant R2, except that for recombinant R1, the 12,000g supernatant was further clarified by centrifugation at 100,000g for 1 hour at 4° C. to remove aggregated proteins. The soluble fraction (up to 35 mg of total protein) was loaded on an affinity column having the affinity matrix coupled to the dodecapeptide (STSYAGAVVNDL; SEQ ID NO:4), corresponding to the C terminus of the HSV R2 subunit; and recombinant R1 was purified as previously described (Paradis et al., 1991, *J. Biol. Chem.* 266:9647–9651) with some modifications. Protein concentration was determined by the Coomassie blue method, and the degree of purity of recombinant R1 (>95%) was assessed by the determination of the amino acid content.

The level of expression of recombinant R1 in Bac-R1-infected Sf9 cells was found to be much higher than that obtained for recombinant R2 with Bac-R2. Indeed, the level of recombinant R1 in a total cell extracts of Bac-R1-infected Sf9 cells at the peak of expression, was very close to the level found in Ad5BM5-R1-infected 293 cells as judged by the SDS-PAGE analysis of Coomassie blue-stained gels. With either Bac-R1 or the Ad recombinants, a time course experiment showed that the steadystate level of total R1 protein reached a plateau at 40–48 hours post-infection and remained constant thereafter. The activity of recombinant R1 was then measured at various time points post-infection to determine the optimal time for harvesting the infected cells. As expected, in Bac-R1- infected Sf9 cells, no R1 activity was detected at 24 hours post-infection and maximum activity was obtained at 48 hours, and this was followed by a reduction at 72 hours which was more or less accentuated from one infection to another. By comparison, the activity of recombinant R1, in either Ad5BM1-R1 or Ad5BM5-R1 infected 293 cells, was readily detectable as early as 16 hours post-infection, and increased steadily for up to 48 hours, and then decreased more or less abruptly at 72 hours. Since no decrease in activity with either Ad or Bac recombinant R2 subunits at 72 hours post-infection was observed, we hypothesized that some post-translational events were controlling the activity of the R1 subunit both in HSV and recombinant virus-infected cells.

As summarized in Table 2, the R1 activity in the crude extracts of Ad5BM5-R1-infected 293 cells at 48 hours post-infection was 3- and 6-fold higher, respectively, than in Ad5BM1-R1-infected 293 cells or Bac-R1-infected Sf9 cells.

TABLE 2

|  | Ad5BM1-R1 | Ad5BM5-R1 |  | Bac-R1 |  |
|---|---|---|---|---|---|
| Hours post-infection | 48 | 48 | 72 | 48 | 72 |
| Activity in crude extract* | 1.1 | 3.3 | 0.67 | 0.5 | 0.25 |
| Yield** total | 15 | 52 | n.d. | n.d. | n.d. |
| soluble | 5.2 | 16 | n.d. | 2.5 | n.d. |

*(U/mg of total protein)
**(mg of R1/$10^9$ infected cells)

Figure 9A:
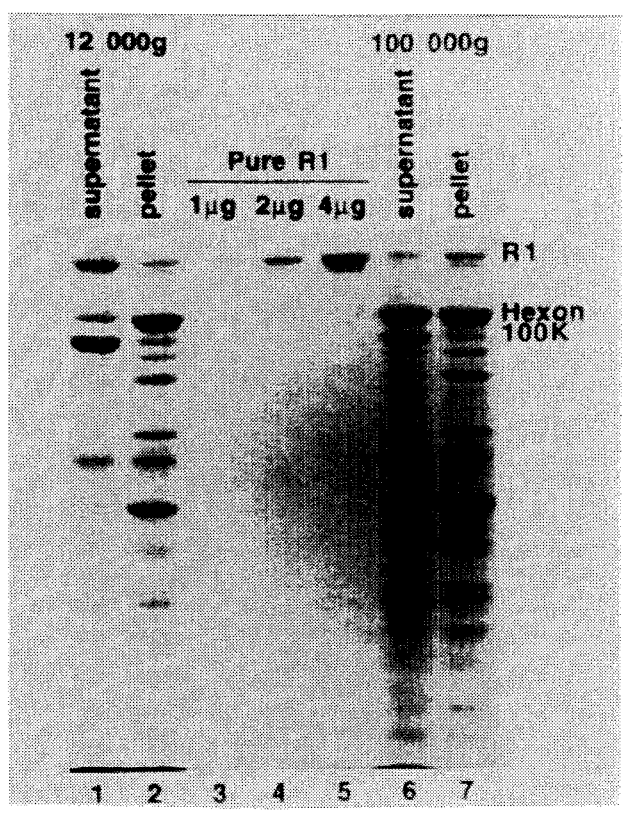
FIG. 9A is a stained SDS-PAGE gel loaded with 1, 2, and 4 μg of >95% pure R1 as standard (lanes 3–5, respectively), and 30 μg of protein from each of the first and second supernatant and pellet; 12,000g pellet and supernatant (lanes 1–2); 100,000g pellet and supernatant (lanes 6–7).

However, in this particular experiment, at 72 hours post-infection, the R1 activity in the crude extracts of Ad5BM5-R1-infected 293 cells was decreased by a factor of 5. When we investigated the reason for this reduction in activity, we found that the decrease in activity correlated well with a decrease in the amount of R1 that was present in the fraction of soluble protein from 48 to 72 hours post-infection, concomitant with an increase in the amount of R1 present in the fraction of proteins found in the pellet. Moreover, even at 48 hours post-infection when the R1 activity was maximal, the majority of the recombinant R1 produced in Ad5BM5-R1-infected 293 cells was found in the 12,000g pellet fraction. This was more precisely quantitated using purified R1 protein as standard (see FIG. 9A). A total cell extract from 4×$10^9$ cells containing 1046 mg of protein was fractionated by an initial centrifugation at 12,000g, followed by a second centrifugation at 100,000g. The total amount of protein was calculated in each fraction, and 30 µg of protein from each of the first and second supernatant and pellet fractions, was resolved by SDS-PAGE and stained with Coomassie blue. In each fraction the R1 protein concentration was measured, and from these data the total amount of R1 was calculated. From a total of 209 mg of R1 (20% of total cellular protein) present in an extract from 4×$10^9$ cells (52 mg/1×$10^9$ cells, Table 2) two thirds (~146 mg) was found in the first pellet and the remaining one third (69.6 mg) in the first supernatant. Upon the second centrifugation, only 6% (4.1 mg) of the soluble R1 was lost in the pellet yielding some 64 mg (16 mg/1×$10^9$ cells, Table 2) of soluble R1 for purification. Thus, it appears that in infected cells, a significant fraction of R1 protein was aggregating presumably as a result of misfolding. However, interestingly enough, the percentage of soluble R1 remained relatively constant in 293 cells infected with either Ad recombinants, as shown in Table 2; 3-fold more total R1 in Ad5BM5-R1-infected cells resulted in a 3-fold increase in activity.

Figure 9B:
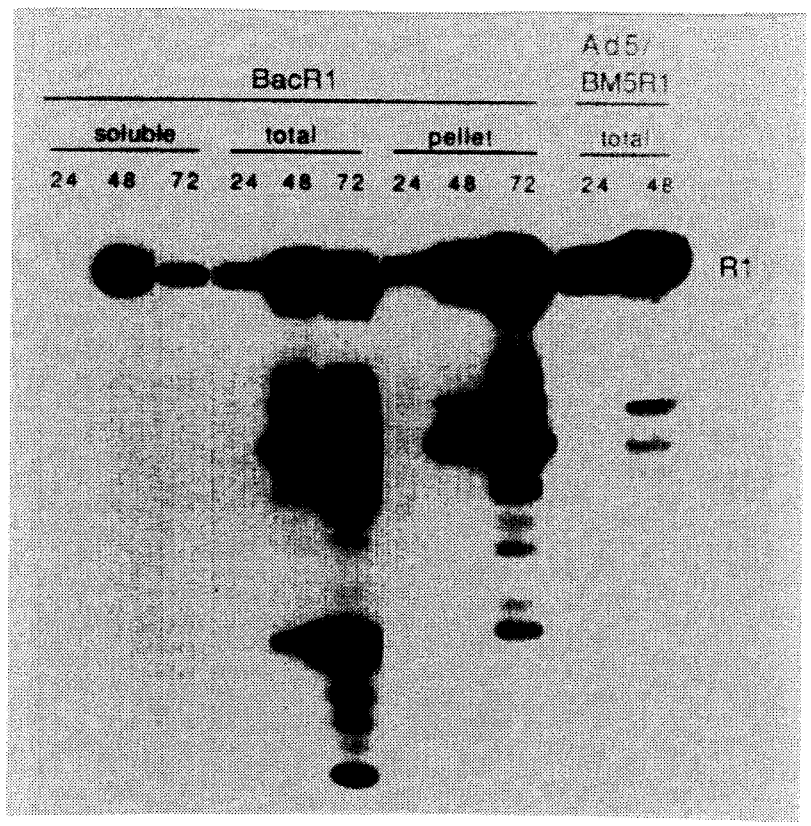
FIG. 9B is a Western blot of Bac-R1-infected Sf9 cells and Ad5BM5-R1-infected 293 cell extracts at various time points post-infection as indicated on the top. Total, soluble, and pellet fractions were prepared as described. Also indicated is the position of the R1 protein.

Although the proportion of soluble R1 in infected Sf9 cells was not precisely quantitated, it was clearly less abundant than in Ad5BM5-R1-infected 293 cells, as shown in the Western blot in FIG. 9B. Moreover, whereas the Bac recombinant R1 found in the soluble fraction was intact (FIG. 9B, first 3 lanes), a significant degradation of the protein was observed in the total protein extract as well as in the insoluble R1 found in the pellet. This is in contrast with the minimal degradation occurring with the Ad expression system (FIG. 9B, last 2 lanes). Thus, in the case of the Bac-R1, the lower than expected activity of R1 in the crude extract, seemed to be explained both by aggregation and degradation of R1 protein in Sf9 cells.

Thus, according to the methods and compositions of the present invention, a novel and improved Ad expression transfer vector can be constructed that allows for the production of recombinant protein to levels of total cellular protein that equal or exceed the level of the most abundant viral late protein, the hexon, and levels that approach the upper limits of the expression system. These high levels of expression were obtained by relocating an enhancer-like sequence to the intron located between the third segment of the Ad tripartite leader and the cloning site in the expression cassette; and expression is further increased by placing an enhancer within a few hundred bp upstream of the MLP transcription start site.

Figure 10:
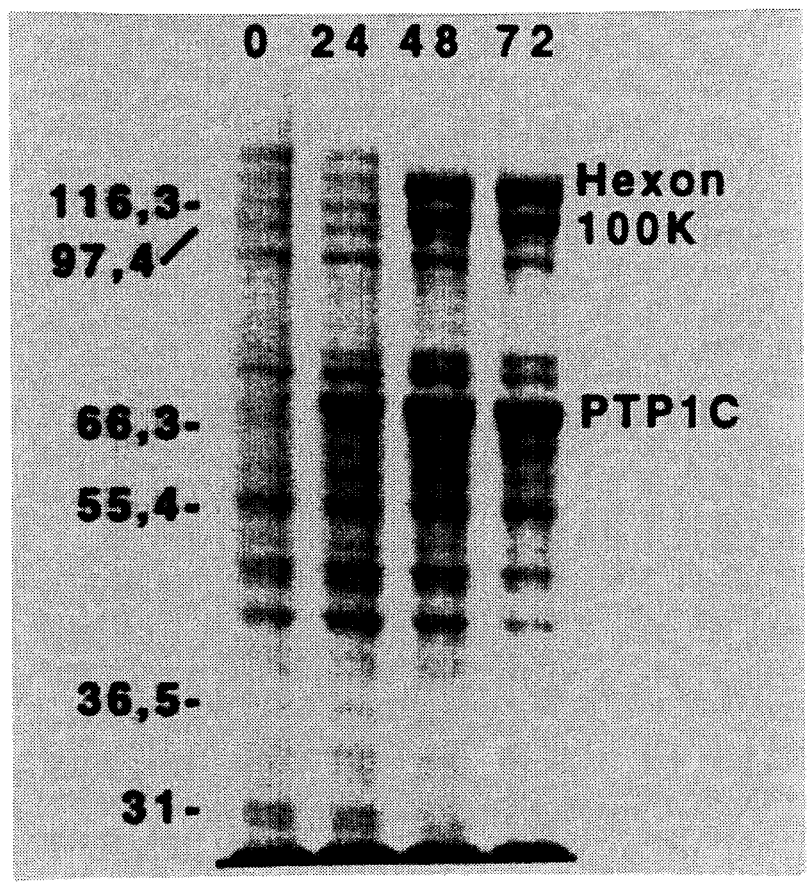
FIG. 10 is a stained SDS-PAGE gel of total proteins produced in 293 cells, infected with Ad5BM5-PTPIC, at 24, 48, and 72 hours. Each lane contains cell extracts from an equal number of cells. Also indicated are molecular weight markers, and the position of hexon, 100K, and PTPIC proteins.

While expression of HSV-2 R1 and R2 ribonucleotide reductase subunits were used to illustrate the enhanced expression of recombinant proteins with the novel and improved vector according to the methods and compositions of the present invention, other cellular genes have been cloned into the vector resulting in expression at comparable high levels. For example, high levels of expression of the PTP1C gene cloned into a vector according to the present invention is illustrated in FIG. 10. A yield of 45 mg/1×10$^9$ cells has been estimated for PTP1C. Also, human R1 and R2 ribonucleotide reductase subunits were expressed in comparable high levels.

It should be understood that while the invention has been described in detail herein, the examples were for illustrative purposes only, and the invention can be embodied otherwise without departing from the principles thereof. Such other embodiments are meant to come within the scope of the present invention as defined by the appended claims.

We claim:

1. An adenovirus transfer vector for introducing a DNA sequence, encoding a recombinant protein, into an adenovirus genome in generating a helper-free adenovirus recombinant, said transfer vector:

(a) contains an expression cassette comprising in sequential order, a first enhancer-like sequence as shown in SEQ ID NO:b 2, a transcriptional promoter, a high efficiency leader, at least one splicing signal, a second enhancer-like sequence as shown in SEQ ID NO:1, a cloning site and a plurality of polyadenylation sites; and (b) provides a means for generating a helper-free adenovirus recombinant, wherein expression of recombinant protein by a mammalian cell infected with the helper-free adenovirus recombinant is at a level of about 10% to about 25% of total cellular proteins.

2. A helper-free adenovirus recombinant made by homologous recombination between the transfer vector of claim 1 containing a DNA sequence encoding a protein, and adenovirus genomic DNA.

3. The transfer vector of claim 1, wherein said transfer vector is pAdBM5, having ATCC Designation 75704, and wherein the first enhancer-like sequence comprises a BK virus enhancer sequence, the transcriptional promoter comprises an adenovirus MLP, the high efficiency leader comprises an adenovirus tripartite leader, and the second enhancer-like sequence comprises adenovirus binding sites R1, R2, and R3.

4. A helper-free adenovirus recombinant made by homologous recombination between the transfer vector of claim 3 containing a DNA sequence encoding a protein, and adenovirus genomic DNA.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 101 nucleotides
        ( B ) TYPE: nucleic acid
        ( C ) STRANDEDNESS: double
        ( D ) TOPOLOGY: linear ( i i ) ORIGINAL SOURCE:
        ( A ) ORGANISM: Adenovirus 5

( i i i ) PUBLICATION INFORMATION:
        ( A ) AUTHORS: Leong, Kahan; Lee, Wes; and Berk, Arnold
        ( B ) TITLE: High-Level Transcription from the Adenovirus Major
            Late Promoter Requires Downstream Binding Sites for
            Late-Phase- Specific Factors
        ( C ) JOURNAL: Journal of Virology
        ( D ) VOLUME: 64
        ( E ) PAGES: 51-60
        ( F ) DATE: January, 1990

( i v ) SEQUENCE DESCRIPTION: SEQ ID NO:1:

```
CCAGCTGTTG  GGGTGAGTAC  TCCCTCTCAA  AAGCGGGCAT  GACTTCTGCG           50

CTAAGATTG  TCAGTTTCCAA  AAACGAGGAG  GATTTGATAT  TCACCTGGCC  C       101
```

( 2 ) INFORMATION FOR SEQ ID NO:2:

( i ) SEQUENCE CHARACTERISTICS:
        ( A ) LENGTH: 68 nucleotides
        ( B ) TYPE: nucleic acid
        ( C ) STRANDEDNESS: single
        ( D ) TOPOLOGY: linear ( i i ) ORIGINAL SOURCE:
        ( A ) ORGANISM: human BK virus ( i i i ) PUBLICATION INFORMATION:
        ( A ) AUTHORS: Berg, David; Walls, Jenna; Grinnell, Brian
        ( B ) TITLE: A variant enhancer/regulatory region from a cloned
            human prototype BK virus genome
        ( C ) JOURNAL: Nucleic Acids Research
        ( D ) VOLUME: 16
        ( E ) PAGES: 9057
        ( F ) DATE: 1988

( i v ) SEQUENCE DESCRIPTION: SEQ ID NO:2:

```
CACAGGGAGG  AGCTGCTTAC  CCATGGAATG  CAGCCAAACC  ATGACCGCAG           50

GAAGGAAAGT  GCATGACT                                                68
```

( 2 ) INFORMATION FOR SEQ ID NO:3:

( i ) SEQUENCE CHARACTERISTICS:
        ( A ) LENGTH: 23 nucleotides
        ( B ) TYPE: nucleic acid
        ( C ) STRANDEDNESS: double
        ( D ) TOPOLOGY: linear ( i i ) ORIGINAL SOURCE: synthesized ( i i i ) SEQUENCE DESCRIPTION: SEQ ID NO:3:

CCATGGATCC GCCGCCGCCA TGG                                      23

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( v i ) ORIGINAL SOURCE: synthesized ( x i ) SEQUENCE DESCRIPTION: SEQ ID NO:4:

Ser Thr Ser Tyr Ala Gly Ala Val Val Asn Asp Leu
1               5                     10      12